United States Patent [19]
Saito et al.

[11] Patent Number: 4,936,307
[45] Date of Patent: Jun. 26, 1990

[54] ULTRASONIC OBSERVATION SYSTEM AND AN ULTRASONIC ENDOSCOPE SYSTEM

[75] Inventors: Yoshitake Saito, Kunitachi; Tatsuo Nagasaki, Yokohama; Takashi Tsukaya, Hachioji; Tsuguhisa Sasai, Hachioji; Akira Hasegawa, Hachioji; Takeaki Nakamura, Hino; Koichi Matsui, Tokyo; Akira Murata, Hachioji; Hiroki Hibino, Hachioji; Yutaka Ohshima, Hachioji; Koji Yamaya, Hachioji; Michio Sato, Hachioji; Akira Suzuki, Hachioji; Koji Kambara, Hachioji; Masaaki Hayashi, Hachioji; Hideo Adachi, Iruma; Hideo Tomabechi, Higashiyamato, all of Japan

[73] Assignee: Olympus Optical Co., Ltd., Tokyo, Japan

[21] Appl. No.: 181,534

[22] Filed: Apr. 14, 1988

[30] Foreign Application Priority Data

| Apr. 20, 1987 | [JP] | Japan | 62-96861 |
| Apr. 30, 1987 | [JP] | Japan | 62-106747 |
| Oct. 22, 1987 | [JP] | Japan | 62-160791[U] |
| Nov. 19, 1987 | [JP] | Japan | 62-290478 |
| Nov. 28, 1987 | [JP] | Japan | 62-298900 |
| Dec. 4, 1987 | [JP] | Japan | 62-305962 |

[51] Int. Cl.$^5$ ............................................. A61B 8/12
[52] U.S. Cl. ........................................ 128/662.06; 128/4
[58] Field of Search .................. 128/660.09, 660.10, 128/662.05, 662.06, 4

[56] References Cited

U.S. PATENT DOCUMENTS

| 4,375,818 | 3/1983 | Suwaki et al. | 128/662.06 |
| 4,479,388 | 10/1984 | Matzuk | 128/660.1 X |
| 4,494,549 | 1/1985 | Namba et al. | 128/662.06 |
| 4,504,760 | 3/1985 | Yamamoto et al. | 310/323 |
| 4,545,441 | 6/1984 | Taniguchi | 310/328 |
| 4,732,156 | 3/1988 | Nakamura | 128/662.06 X |
| 4,756,313 | 7/1988 | Terwilliger | 128/662.06 X |

FOREIGN PATENT DOCUMENTS

| 0046987 | 3/1982 | European Pat. Off. . |
| 3619195 | 6/1986 | Fed. Rep. of Germany . |
| 8303749 | 11/1983 | PCT Int'l Appl. . |

*Primary Examiner*—Francis Jaworski
*Attorney, Agent, or Firm*—Stevens, Davis, Miller & Mosher

[57] ABSTRACT

In a probe for observing an ultrasonic image, which obtains the ultrasonic image of an object to be observed such as a body cavity by means of an ultrasonic transmitting and receiving means, a mechanical scanning operation of the ultrasonic transmitting and receiving means is performed by an ultrasonic driving means, and thus it is possible to obtain a good diagnosis image with no distortion and no flicker because noises of the driving means can be reduced.

Therefore, an ultrasonic endoscope system and an ultrasonic video endoscope system etc. which utilize the probe mentioned above can display a good ultrasonic image and a good optical image.

28 Claims, 21 Drawing Sheets

FIG.6A
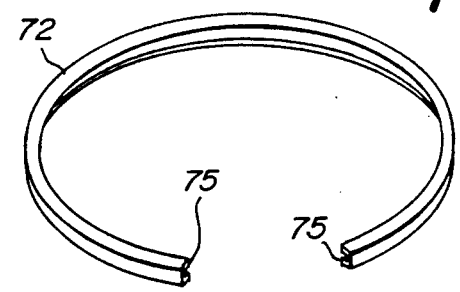
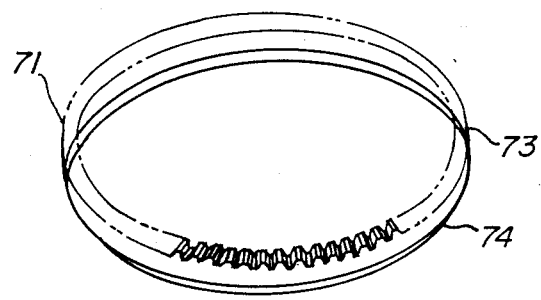
FIG.6B
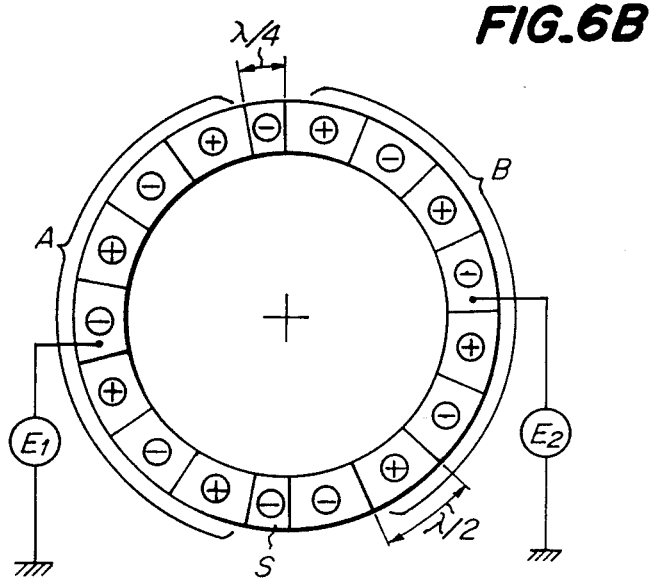

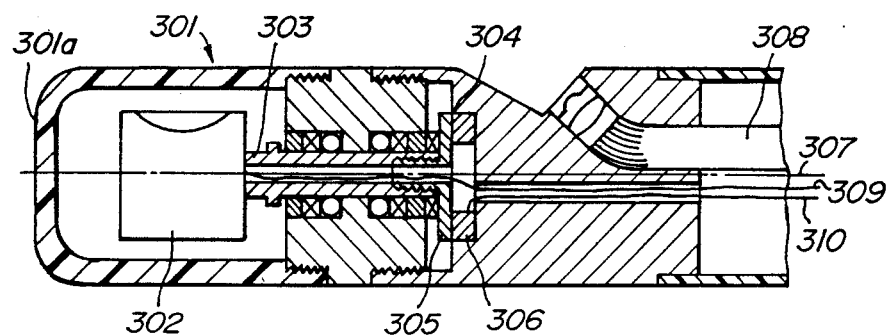
FIG._18
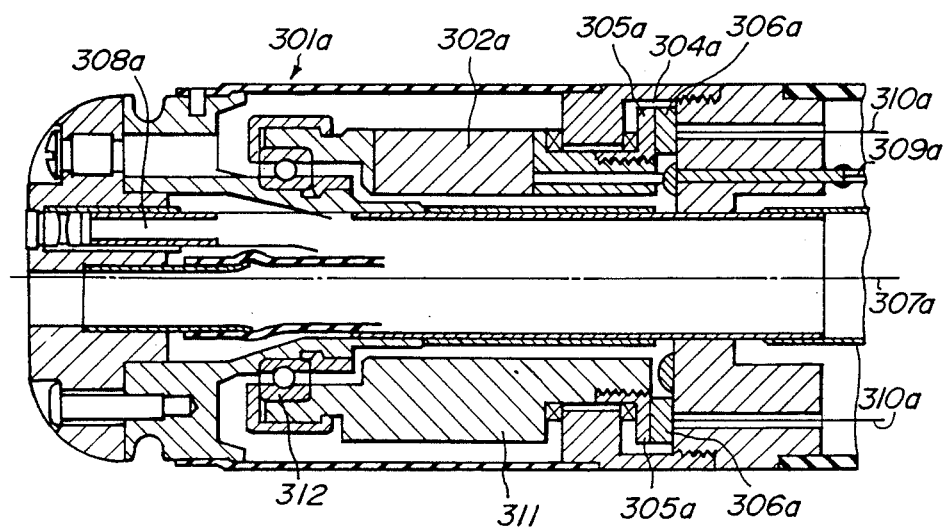
FIG._19

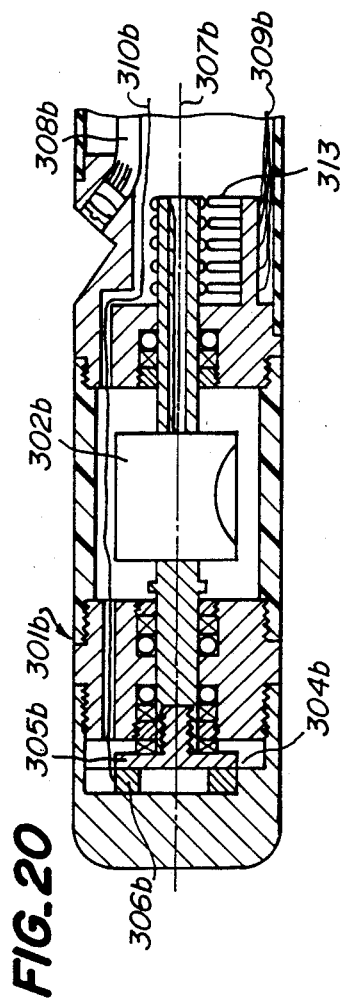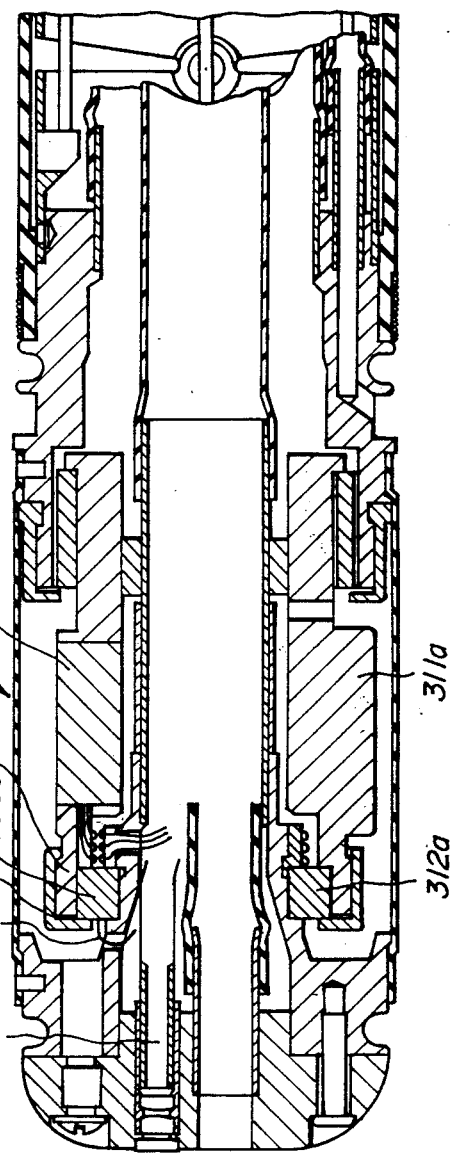

ULTRASONIC OBSERVATION SYSTEM AND AN ULTRASONIC ENDOSCOPE SYSTEM

BACKGROUND OF THE INVENTION

1. Field of the Invention

The present invention relates to a probe for an ultrasonic endoscope which observes an object inside a body cavity by using an ultrasonic wave, and relates to an ultrasonic endoscope system, an ultrasonic observation system and an ultrasonic video endoscope system, all of which utilize the probe mentioned above.

2. Related Art Statement

An ultrasonic endoscope system utilizing a probe has been known for example from Japanese Patent Laid-Open Publication No. 57-190,552, wherein an object inside the body cavity is diagnosed with an ultrasonic wave by rotating mechanically an ultrasonic vibrating element arranged in a distal end of an insertion section of the probe by means of a driving member arranged apart from the insertion section.

FIG. 1 is a schematic view showing an embodiment of the probe disclosed in the Japanese Patent Laid-Open Publication No. 57-190,552. In this embodiment, A is the insertion section and B is the driving member.

In a distal end of the insertion section A, an ultrasonic vibrating element 1 is rotatably secured by means of a bearing 2, and a tip portion of a flexible shaft 3 is connected to the ultrasonic vibrating element 1. The flexible shaft 3 is held in a flexible outer tube 5 through a liquid paraffin 4 and a proximal end of the flexible shaft 3 is introduced to the driving member B.

The driving member B comprises an electric motor 6 as a driving means, a gear box 7 for decelerating a rotation speed of the electric motor 6, an output shaft 8 including a shaft member 8a and a bearing 8b, for transmitting the decelerated rotation to the flexible shaft 3, and a potentiometer 9 arranged to the electric motor 6.

The prior art ultrasonic endoscope system mentioned above has drawbacks mentioned below. In the case that a patient swallows the insertion section A of the probe, it is a matter of course that the patient can easily swallow the insertion section A if it is thin. However, if the flexible shaft 3 is made thinner so as to make the insertion section A thin, kinks are liable to occur on the flexible shaft 3, and thus the rotation of the electric motor 6 is not transmitted accurately. That is to say, if the above kinks are generated, the rotation of the ultrasonic vibrating element 1 is decreased correspondingly, and thus if an amount of kinks reaches to a predetermined level, the rotation of the ultrasonic vibrating element 1 is increased over a normal rotation level. As a result, a time-angle characteristic of the rotation of the ultrasonic vibrating element 1 is vibrated as shown in FIG. 2 by a solid line. Moreover, characteristics during respective scanning periods T1, T2 . . . are varied one another. Therefore, as shown in FIG. 3 by a solid line M and a dotted line N, the clinical image obtained by the known ultrasonic endoscope system becomes large or small with respect to the normal one, and thus an accurate diagnosis is not realized.

Further, as clearly understood from FIG. 2, since the time-angle characteristic is varied pulsatory as shown by a solid line with respect to the normal linear variation as shown by a dotted line and this pulsatory variation occurs irregularly, a starting point of the next scanning operation is varied. As a result, the obtained image position is varied correspondingly, For example, this variation becomes at a rate of $\Delta\theta = 20°$, and thus accurate diagnosis cannot be achieved.

To eliminate the distortion and the positional variation in the clinical image, if the flexible shaft 3 is made thick and stiff, the following disadvantages occur. If the flexible shaft 3 is made thick and stiff, the kinks remain on the shaft 3 because it is normally long. Therefore, the rotation of the motor 6 becomes somewhat stable, but the scanning characteristic of the ultrasonic vibrating element 1 is not linear but still pulsatory. Moreover, in this case, since the insertion section A becomes large and stiff (not flexible), the patient does not swallow the insertion section A easily and an operationability of the insertion section A in the body cavity becomes bad.

Contrary to this, since use is made of a D.C. motor as the electric motor 6, so-called brush noise is generated on a signal line of the ultrasonic vibrating element 1. As a result, a flicker effect is generated on an image displayed on a CRT by a scanning operation of the ultrasonic vibrating element 1. This flicker effect can be eliminated by a noise reduction circuit such as a filter. However, in this case, since it is necessary to arrange a specific noise reduction circuit, the ultrasonic endoscope system becomes large and complicated, and further a reliability becomes low.

Further, in the known ultrasonic endoscope system, since use is made of the electric motor which is large in size and complicated in mechanism, there is a drawback that the operationability thereof becomes bad.

SUMMARY OF THE INVENTION

The object of the present invention is to eliminate the drawbacks mentioned above and to provide a probe for an ultrasonic endoscope which car obtain a good ultrasonic image with no distortion and no flicker in an easy and reliable manner.

The another object of the invention is to provide an ultrasonic endoscope system which can display a good ultrasonic image and a good optical image without generating a distortion and a flicker.

The still another object of the invention is to provide an ultrasonic observation system which can display a good ultrasonic image in an easy manner without generating a distortion and a flicker.

The still another object of the invention is to provide an ultrasonic video endoscope system utilizing a solid state image pick-up device which can display a good ultrasonic image and a good optical image without generating a distortion and a flicker.

According to the invention, a probe for observing an ultrasonic image comprises an insertion section for being inserted into an object to be observed, an ultrasonic transmitting and receiving means provided in a distal end portion of said insertion section for transmitting an ultrasonic wave to the object and for receiving the ultrasonic wave reflected on the object, in which the received ultrasonic wave is converted into an electric signal, and an ultrasonic driving means for driving said ultrasonic transmitting and receiving means to effect a mechanical scanning operation using the ultrasonic wave with respect to the object to be observed.

According to the invention, a probe for observing an ultrasonic image comprises an insertion section for being inserted into an object to be observed, an ultrasonic transmitting and receiving means provided in a distal end portion of said insertion section for transmitting an ultrasonic wave to the object and for receiving the ultrasonic wave reflected on the object, in which the received ultrasonic wave is converted into an electric signal, and an ultrasonic driving means for driving said ultrasonic transmitting and receiving means to effect a mechanical scanning operation using the ultrasonic wave with respect to the object to be observed.

According to the invention, an ultrasonic endoscope system comprises a probe having an insertion section for being inserted into an object to be observed; an ultrasonic transmitting and receiving means provided in a distal end portion of said insertion section for transmitting an ultrasonic wave to the object and for receiving the ultrasonic wave reflected on the object, in which the received ultrasonic wave is converted into an electric signal; an ultrasonic driving means for driving said ultrasonic transmitting and receiving means to effect a mechanical scanning operation using the ultrasonic wave with respect to the object to be observed; and an observation means for obtaining an optical image of the object through said insertion section, and a display device having means for displaying an ultrasonic image obtained from said ultrasonic transmitting and receiving means and means for displaying the optical image obtained from said observation means.

According to the invention, an ultrasonic image observation system comprises a probe having an ultrasonic transmitting and receiving means for transmitting an ultrasonic wave to an object to be observed and for receiving the ultrasonic wave reflected on the object, in which the received ultrasonic wave is converted into an electric signal; and an ultrasonic driving means for driving said ultrasonic transmitting and receiving means to effect a mechanical scanning operating using the ultrasonic wave with respect to the object to be observed, and a display device for displaying an ultrasonic image obtained from said ultrasonic transmitting and receiving means.

According to the invention, an ultrasonic video endoscope system comprises a video probe having an insertion section for being inserted into an object to be observed; an ultrasonic transmitting and receiving means provided in a distal end portion of said insertion section for transmitting an ultrasonic wave to the object and for receiving the ultrasonic wave reflected on the object, in which the received ultrasonic wave is converted into an electric signal; an ultrasonic driving means for driving said ultrasonic transmitting and receiving means to effect a mechanical scanning operation using the ultrasonic wave with respect to the object to be observed; and an observation means including a light guide extended in said insertion section, an objective lens provided in the distal end portion of said insertion section and a solid state image sensor, and a display device having means for displaying an ultrasonic image obtained from said ultrasonic transmitting and receiving means and means for displaying the optical image obtained from said observation means.

BRIEF DESCRIPTION OF THE DRAWINGS

FIG. 6A is a perspective view showing a construction of an ultrasonic motor according to the invention;

FIG. 6B is a schematic view illustrating an electrode construction of the ultrasonic motor shown in FIG. 6A;

FIGS. 18 to 21 are cross sectional views depicting an eighth embodiment to an eleventh embodiment of the probe according to the invention respectively;

DESCRIPTION OF THE PREFERRED EMBODIMENTS

Figure 1:
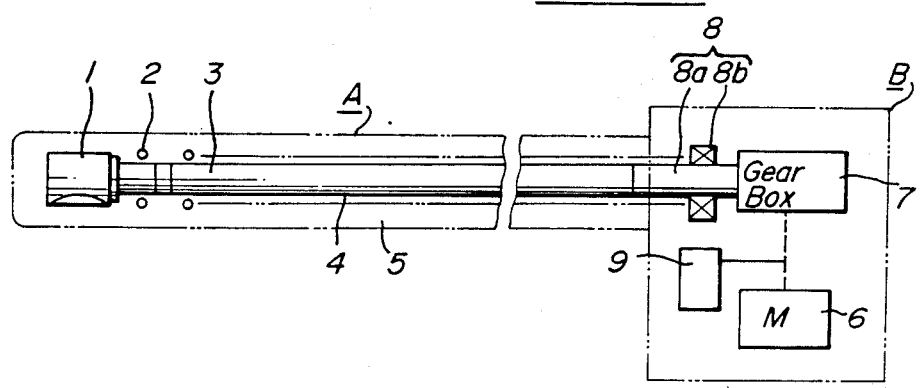
FIG. 1 is a schematic view showing an embodiment of a known probe of an ultrasonic endoscope.
Figure 2:
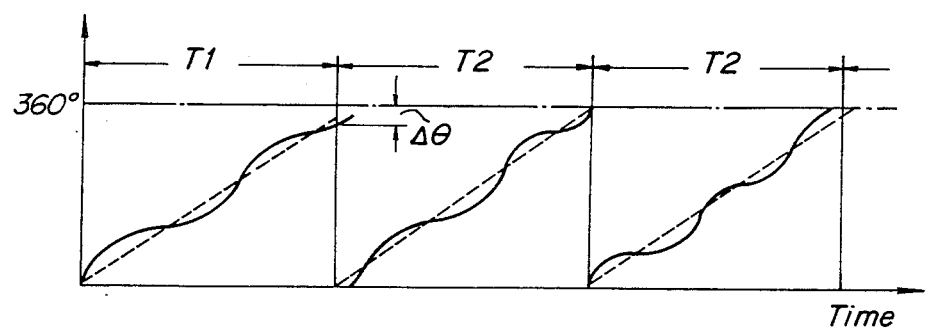
FIG. 2 is a graph for explaining a scanning characteristic of the known probe shown in FIG. 1.
Figure 3:
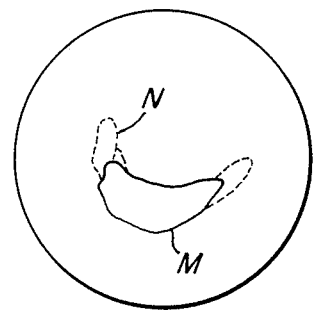
FIG. 3 is a schematic view showing a clinical image obtained from the known probe.
Figure 4:
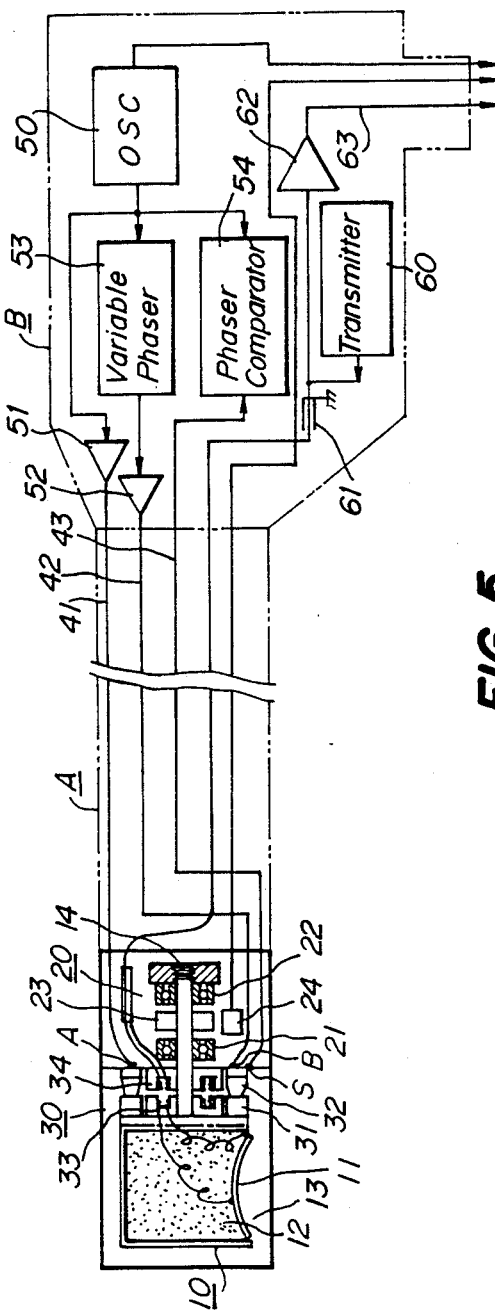
FIG. 4 is a schematic view illustrating a first embodiment of a probe of an ultrasonic endoscope according to the invention.

FIG. 4 is a schematic view showing a first embodiment of a probe of an ultrasonic endoscope according to the invention, wherein an ultrasonic motor is arranged in a distal end of an insertion section. In FIG. 4, a numeral 10 is an ultrasonic vibrating element secured in a distal end of an insertion section A. The ultrasonic vibrating element 10 comprises a vibration plate 11 and a damper member 12, and an acoustic medium 13 is filled around the ultrasonic vibrating element 10. A rotation shaft 14 arranged at one end of the ultrasonic vibrating element 10 is rotatably secured by a bearing member 20.

The bearing member 20 is constructed by a pair of bearings 21 and 22. A rotation detection member 23 is secured to the rotation shaft 14 at a position between the bearings 21 and 22, and a rotation start pulse detection sensor 24 is secured to the rotation shaft 14 at a position opposite to the rotation detection member 23. Moreover, an ultrasonic motor 30 is arranged between the bearing member 20 and the ultrasonic vibrating element 10.

The ultrasonic motor 30 comprises a rotor 31 secured to one end of the ultrasonic vibrating element 10 and rotatably arranged around the rotation shaft 14 and a stator 32 secured to one end of the bearing member 20 and rotatably arranged around the rotation shaft 14, and the rotor 31 is brought into contact with the stator 32 under pressure. Rotary transformer elements 33 and 34 for supplying transmitting and receiving signals in a non-contact manner are arranged at a center of the rotor 31 and the stator 32 respectively in an opposite and non-contact manner. In the ultrasonic motor 30, a pair of electrodes of the stator 32 and an earth electrode are connected respectively to one ends of feeders 41, 42 and 43 extended inside the insertion section A. A coil of the first rotary transformer element 34 is connected to one end of a signal transmission line 44 extended also inside the insertion section A. The other ends of the feeders 41, 42 and 43 and the signal transmission line 44 are introduced to an operation section B.

The operation section B comprises a driving member of the ultrasonic vibrating element 10 and a signal control member. The driving member comprises an oscillator 50 for driving the ultrasonic motor 30, an amplifier 51 for amplifying an output of the oscillator 50 and for supplying the amplified signal through the feeder 41, a variable phaser 53 for shifting the output of the oscillator 50 by $\pi/2$, an amplifier 52 for amplifying an output of the variable phaser 53 and for supplying the amplified signal through the feeder 42, and a phase comparator 54 for comparing a rotation phase of the ultrasonic motor 30 obtained through the feeder 43 with an output phase of the oscillator 50 and for supplying the phase difference to the variable phaser 53 as a feedback signal. Moreover, the signal control member comprises a transmitter 60, a signal transmitting and receiving member 61 for supplying an output signal of the transmitter 60 through the signal transmission line 44 and for receiving a signal reflected on the object, a pre-amplifier 62 for amplifying the reflect signal obtained from the signal transmitting and receiving member 61, and a signal output line 63 for supplying an output signal of the pre-amplifier 62.

In this embodiment, a liquid paraffin is filled around the bearings 21 and 22 of the bearing member 20, the rotation detection member 23, the detection sensor 24 and the ultrasonic motor 30. Since the liquid paraffin has a lubricity and an insulation function, it is no problem to immerse the motor etc. therein. In this case, it is necessary to effect a mold on lead wires etc.

Figure 5:
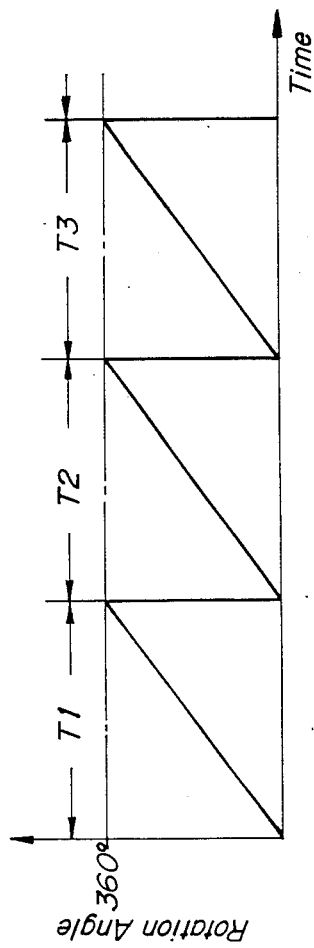
FIG. 5 is a graph for explaining a scanning characteristic of the probe shown in FIG. 4.

According to the first embodiment mentioned above, since the ultrasonic vibrating element 10 arranged rotatably in the distal end of the insertion section A is directly driven by the ultrasonic motor 30 arranged near the ultrasonic vibrating element 10, it is not necessary to use the flexible shaft 3 for driving the ultrasonic vibrating element 1 as usual. Therefore, since use is made of electric lines only for the connection cable between the ultrasonic vibrating element 10 and the operation section B, it is possible to make a diameter of the insertion section A small and thus the flexibility of the insertion section A can be maintained. In this case, the patient can swallow the insertion section A easily and the operation of the insertion section A in the body cavity can be made easy. Moreover, since the rotation variation of the ultrasonic vibrating element due to the kinks of the flexible shaft can be reduced, the scanning operation of the ultrasonic vibrating element 10 can be made accurate and stable as shown in FIG. 5. As a result, good clinical images with no distortion can be obtained. Further, since the brush noise of the electric motor is not generated in the signal transmission line 44, good clinical images with no flicker can be obtained. Moreover, since it is not necessary to use the mechanical members such as D.C. motor 6, gear box 7, and potentiometer 9, the operation section B arranged outside the body cavity can be made small.

Figure 7:
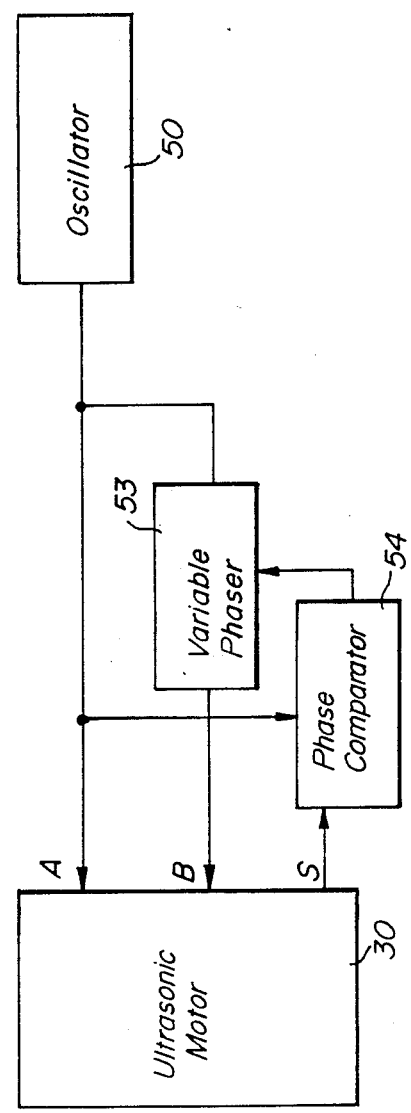
FIG. 7 is a block diagram depicting a circuit of the ultrasonic motor shown in FIG. 4.

FIG. 6A is a perspective view showing a construction of the ultrasonic motor according to the invention. In this embodiment, the ultrasonic motor comprises a stator member 71 for generating a bending vibration due to the ultrasonic wave, and a rotor member 72 arranged in contact with the stator member 71. The stator member 71 comprises a metal ring 73 and a piezoelectric ceramic element 74. Then, the stator member 71 is vibrated in a longitudinal direction by applying a voltage with high frequency over 20 KHz to the piezoelectric ceramic element 74. This vibration of the metal ring 73 proceeds in a circumferential direction, and thus the rotor member 72 is rotated in an inverse direction with respect to the circumferential direction mentioned above. In this embodiment, use is made of the metal ring 73 made of Ni 36%-Fe 64% alloy and the rotor member 71 made of aluminum alloy, and $Al_2O_3$ layer is arranged on the rotor member 71 opposite to the metal ring 73. Since a contact surface 75 of the rotor member 72 is constructed by a flange-shape spring vibrating in the longitudinal direction, the vibration of the stator 71 in the longitudinal direction can be absorbed preferably. Positions of electrodes A and B are shifted by $\lambda/4$ as shown in FIG. 6B. An electrode S observes a resonance state of the bending vibration generated from electrodes A and B respectively. FIG. 7 shows a block diagram illustrating a circuit construction of the ultrasonic motor shown in FIG. 4.

Figure 8:
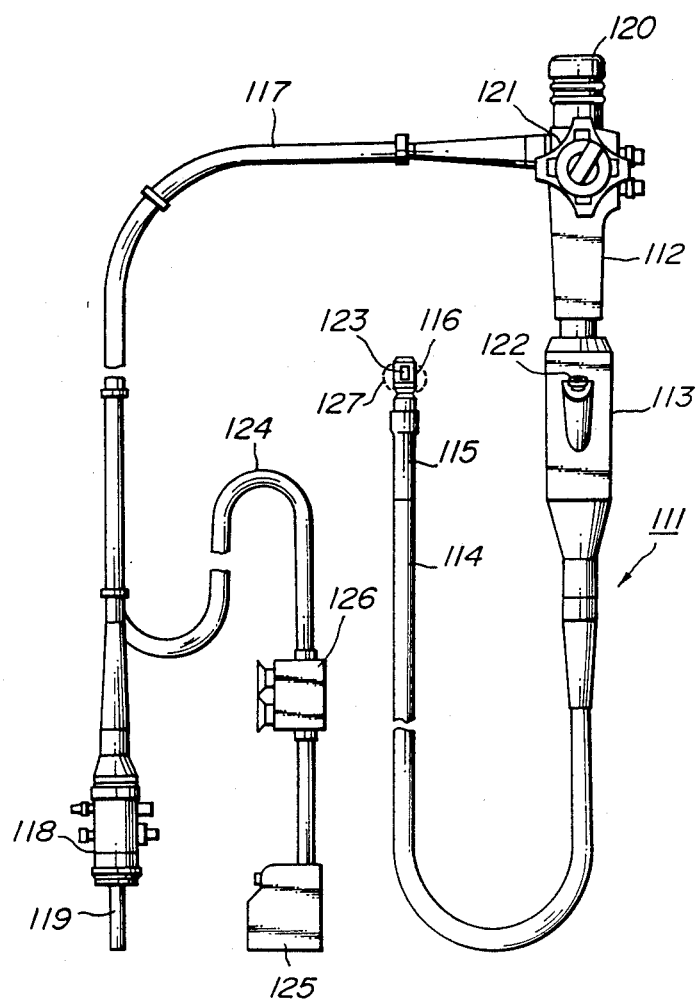
FIG. 8 is a schematic view showing a second embodiment of a probe of an ultrasonic endoscope according to the invention.

FIG. 8 is a schematic view showing a second embodiment of the probe of the ultrasonic endoscope according to the invention. In this embodiment, an endoscope 111 comprises an operation section 112 in which various operation members are arranged, a drive section 113 for driving the ultrasonic vibrating element, and an insertion section 114. A distal hard portion 116 is arranged via a flexible portion 115 at a distal end of the insertion section 114. The operation section 112 has a universal code 117 and a connector 118 is arranged at a distal end of the universal code 117. The connector 118 is to be connected to a light source unit, and thus one end portion of a light guide 119 is projected.

In this embodiment, various members such as light guide, image guide, forceps channel, air supply channel are arranged inside the insertion section 114, and thus an object in the body cavity can be observed by an eyepiece arranged in the operation section 112. This construction is widely known in a field of the endoscope, and thus detail explanations are omitted here. Further, an operation knob 121 for bending the flexible portion 115 is arranged in the operation section 112, and the distal end of the insertion section 114 can be moved in the body cavity at will by operating the operation knob 121. Moreover, an opening 122 of the forceps is arranged in the drive section 113.

An ultrasonic vibrating element 123 is arranged in the distal hard portion 116 of the insertion section 114, and a distal end of the rotation shaft extended in the insertion section 114 is secured to the ultrasonic vibrating element 123. This rotation shaft is extended toward the drive section 113 and is rotated by an ultrasonic motor arranged in the drive section 113. On the other hand, cables connected to the ultrasonic vibrating element 123 are extended in the rotation shaft and further in the universal code 117. Further, these cables are introduced to a connector 125 through a code 124 divided from the universal code 117, and the connector 125 is to be connected to an ultrasonic observation device. Moreover, an amplifier 126 for the repeating operation is arranged in the middle of the code 124. A balloon 127 is detachably arranged outside the distal hard portion 116 as shown in the dotted line, and the balloon 127 is expanded by means of waters so as not to reduce the energy of ultrasonic wave in the body cavity.

Figure 9:
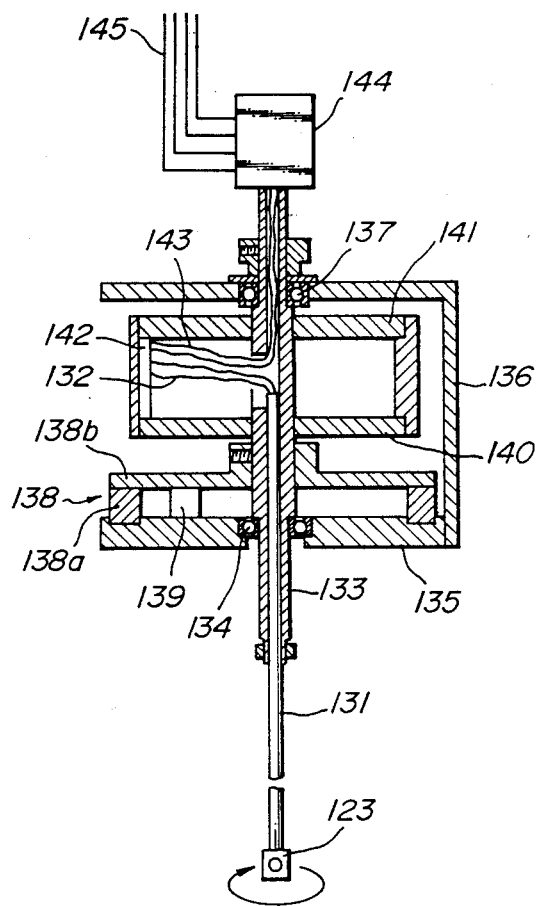
FIG. 9 is a cross sectional view illustrating a driving portion of the second embodiment shown in FIG. 8.

FIG. 9 is a cross sectional view showing the drive section 113 of the second embodiment shown in FIG. 8. In this embodiment, a rotation shaft 131 connected to the ultrasonic vibrating element 123 is constructed by a flexible and cylindrical tube, and a cable 132 connected electrically to the ultrasonic vibrating element 123 is inserted and extended in the rotation shaft 131. The rotation shaft 131 is secured to a sleeve 133 which is rotatably secured to a base 135 via a bearing 134. A supporting member 136 is fixed to the base 135, and the sleeve 133 is also rotatably secured to the supporting member 136 via a bearing 137. An ultrasonic motor 138 is arranged between the base 135 and the sleeve 133. That is to say, a ring-shaped stator 138a is secured to the base 135, and a rotor 138b cooperative with the stator 138a is secured to the sleeve 133. Moreover, a rotation position detector 139 is secured to the base 135 so as to detect a mark arranged on the rotor 138b at a position opposite to the base 135. In this manner, a rotation position of the sleeve 133 i.e. the rotation shaft 131 is detected. Further, flanges 140 and 141 are fixed to the sleeve 133, and a receiving amplifier 142 is arranged between the flanges 140 and 141. The cable 132 is connected to the receiving amplifier 142 so as to amplify the signal supplied from the ultrasonic vibrating element 123. The signal amplified by the receiving amplifier 142 is supplied to a rotary contact box 144 through a cable 143 arranged in the sleeve 133 and is further supplied to a cable 145 through for example a slip ring contact.

The stator 138a of the ultrasonic motor 138 has electrodes divided into a few parts, a ring-shaped piezoelectric elements and a ring-shaped elastic member, but in FIG. 9 all members are shown as the stator. When a driving voltage having a predetermined phase is applied to the piezoelectric element, the piezoelectric element is vibrated and the elastic member is also vibrated as a wave, and then the rotor 138b brought into contact with the elastic member is rotated. Since the rotor 138b is secured to the sleeve 133 which is secured to the rotation shaft 131, the rotation shaft 131 is rotated and thus the ultrasonic vibrating element 123 connected to the distal end of the rotation shaft 131 is also rotated.

In this manner, if use is made of the ultrasonic motor 138, and the stator 138a and the rotor 138b are arranged coaxially to the rotation shaft 131, a dimension of the whole drive section can be made small. Moreover, since the rotor 138b is directly connected to the rotation shaft, it is not necessary to use power supply mechanisms such as gear, timing belt, a total amount of mechanisms to be used can be reduced. Further, since mechanisms of the ultrasonic motor are not arranged on an axis of the rotation shaft, the cable can be arranged in the rotation shaft easily and the rotary contact box 144 can be arranged on the axis of the rotation shaft. Therefore, the construction can be simplified.

Figure 10:
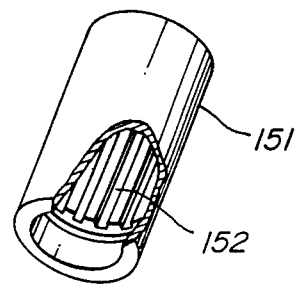
FIGS. 10 and 11 are schematic views illustrating another embodiment of the driving portion respectively.
Figure 11:
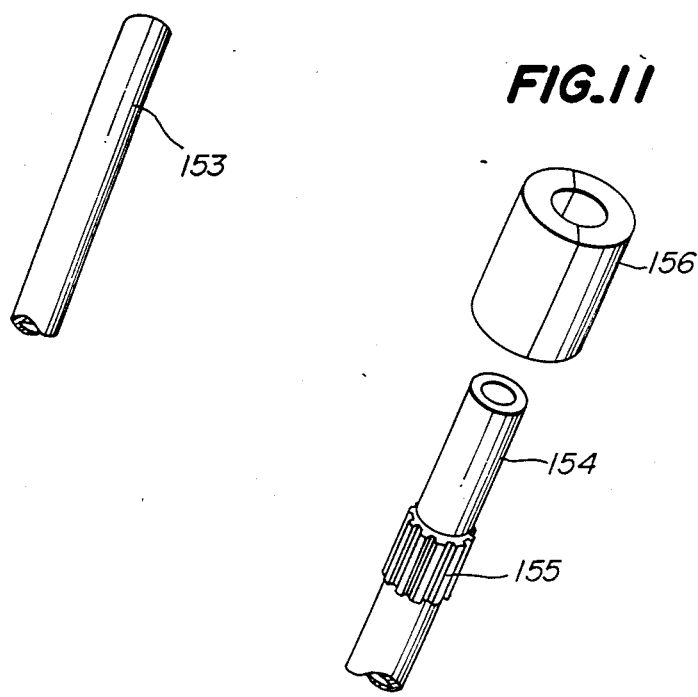

The present invention is not limited to the second embodiment mentioned above, but various modifications are possible. For example, in the second embodiment mentioned above, the stator and the rotor have the ring-shape, but it is possible to use a circular plate stator and rotor each having a hole at its center. Further, as shown in FIG. 10, use may be made of the ultrasonic motor wherein a cylindrical stator 152 comprising electrodes, piezoelectric element and elastic member is secured to an inner surface of a cylinder 151 and a rotor 153 having a sleeve shape is inserted into the cylindrical stator 152. Further, as shown in FIG. 11, use may be made of the ultrasonic motor wherein a stator 155 is secured to an outer surface of a sleeve 154 connected to the rotation shaft, and cylinders 156 divided into two parts are arranged around the stator 155 to rotate the sleeve 154.

Figure 12:
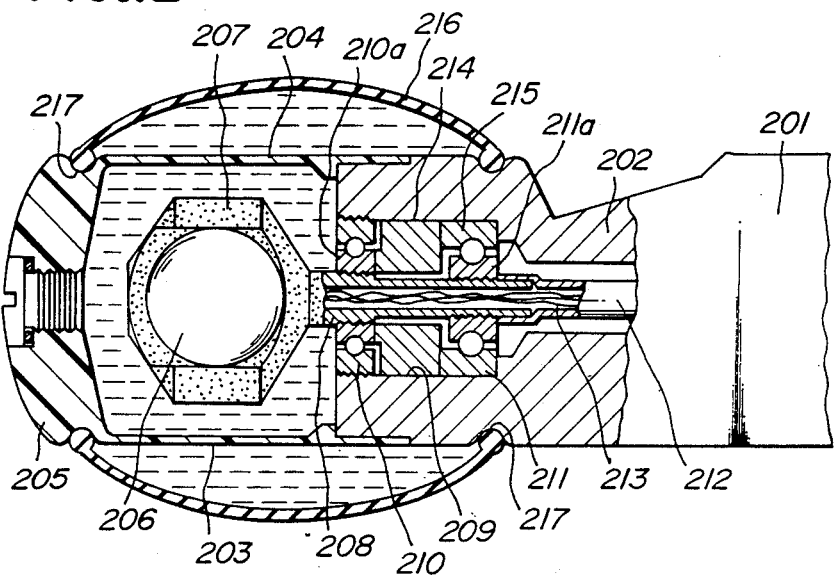
FIGS. 12 and 13 are cross sectional views depicting a third and fourth embodiments of the probe according to the invention respectively.

FIG. 12 is a cross sectional view showing a third embodiment of the probe according to the invention. In this embodiment, a numeral 201 is an insertion section for being inserted into the body cavity, and an ultrasonic scanning head 203 is arranged in a distal end portion 202 of the insertion section 201. The ultrasonic head 203 comprises a cylindrical cover 204 projected from the distal end portion 202 in an axis direction of the insertion section 201. One end of the cover 204 is connected to an outer surface of the distal end portion 202, and the other end of the cover 204 is closed by a tip wall portion 205. Moreover, an ultrasonic vibrating element 206 for transmitting and receiving the ultrasonic wave is accommodated in an inner space of the cover 204.

A tubular rotation shaft 208 is projected integrally from a supporting member 207 for covering the ultrasonic vibrating element 206, and the rotation shaft 208 is introduced into a hole 209 arranged in a tip surface of the distal end portion 202. In the hole 209, ball bearings 210 and 211 are arranged to support the rotation shaft 208 rotatably, and inner lathes 210a and 211a of the ball bearings 210 and 211 are screwed in an outer surface of the rotation shaft 208 to be rotated integrally with the rotation shaft 208.

Moreover, a signal cable 213 for transmitting and receiving a signal supplied from the ultrasonic vibrating element 206 is inserted into the rotation shaft 208 and a protection tube 212 connected to the rotation shaft 208, and the signal cable 213 is connected to an ultrasonic transmitting and receiving device not shown arranged at a proximal end of the insertion section 201.

In the hole 209 of the distal end portion 202, an ultrasonic motor 214 having a ring shape for rotating the ultrasonic vibrating element 20 is installed. The ultrasonic motor 214 comprises an ultrasonic vibrator 215 having a ring shape. In the hole 209, the ultrasonic vibrator 215 is arranged between the ball bearings 210 and 211, and is arranged coaxially with respect to the rotation shaft 208. Then, one end surface of the ultrasonic vibrator 215 is coaxially brought into contact with the inner lathe 210a of the ball bearing 210 positioned at a side of the ultrasonic vibrating element 206, and the ultrasonic vibrator 215 is connected to an operation section of the ultrasonic motor 201 through a driving cable not shown extended in the insertion section 201.

Therefore, by actuating the operation section of the ultrasonic motor and by vibrating the ultrasonic vibrator 215, a wave moved along the circumferential direction is generated between the ultrasonic vibrator 215 and the inner lathe 210a, and the inner lathe 210a is rotated. In this embodiment, the inner lathe 210a of the ball bearing 210 is served as the rotor of the ultrasonic motor 214. Further, in the inner space of the cover 204 which accommodates the ultrasonic vibrating element 206, a liquid having good transmission faculty for the ultrasonic wave is filled.

Moreover, a balloon 216 made of an elastic material such as a rubber is arranged around an outer surface of the ultrasonic scanning head 203. The balloon 216 is secured to the ultrasonic scanning head 203 by arranging front and rear edge portions into recesses formed on outer surfaces of the cover 204 and the distal end portion 202. A deaerated water is filled in the balloon 216 through an air supply path (not shown)arranged in the insertion section 201, and the balloon 216 is expanded.

In the construction mentioned above, the ultrasonic vibrator 215 of the ultrasonic motor 214 is arranged coaxially to an outer surface of the rotation shaft 208 connected to the ultrasonic vibrating element 206, and one end surface of the ultrasonic vibrator 215 is brought into contact with the inner lathe 210a of the ball bearing 210 rotated integrally with the rotation shaft 208. Therefore, if the ultrasonic vibration is applied to the ultrasonic vibrator 215, a wave moved along the circumferential direction is generated between the ultrasonic vibrator 215 and the inner lathe 210a, and the inner lathe 210a is rotated. Since the rotation of the inner lathe 210a is transmitted to the ultrasonic vibrating element 206 through the rotation shaft 208, the ultrasonic vibrating element 206 is rotated in the space of the cover 204. Therefore, the ultrasonic scanning operation is performed by receiving an echo of the ultrasonic wave transmitted from the ultrasonic vibrating element 206 by means of the ultrasonic vibrating element 206.

In this case, since the ultrasonic motor 214 wherein the rotation shaft 208 is rotated by utilizing the wave generated between the ultrasonic vibrator 215 and the inner lathe 210a has a large torque in low rotation speed as compared with the electric motor, it is not necessary to use a specific speed reducer, and thus the ultrasonic motor 214 can be installed in the distal end portion 202 in a compact manner.

Moreover, since the ultrasonic motor is constructed by only two parts of the ring-shaped ultrasonic vibrator 215 and inner lathe 210a and thus it is light in weight and small in dimension, it is possible to make the drive section for rotating the ultrasonic vibrating element 206 small as compared with the known ultrasonic endoscope.

Therefore, it is possible to install directly the ultrasonic motor 214 in the distal end portion 202 without making a dimension of the distal end portion 202 large, and thus the insertion section 201 can be made light in weight. As a result, the patient can swallow the insertion section 201 easily and the operationability of the insertion section can be improved.

Figure 13:
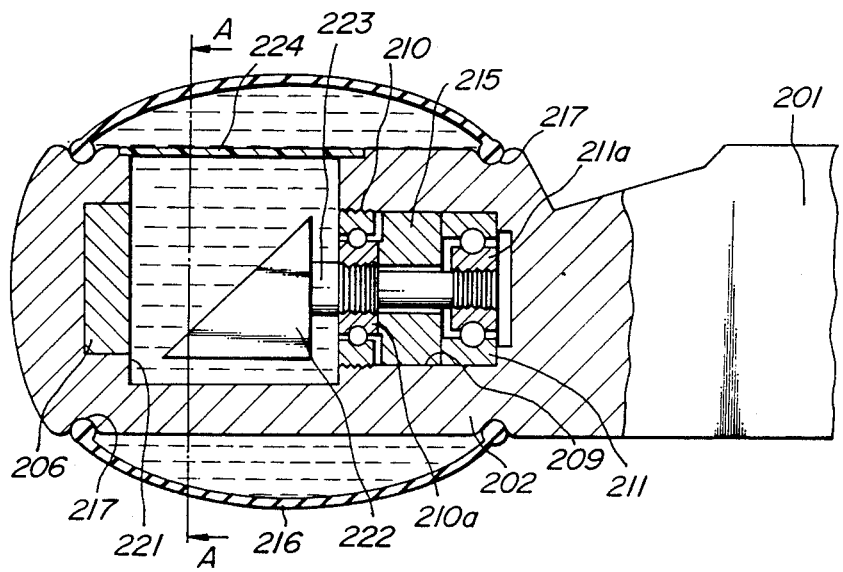

FIG. 13 is a cross sectional view showing a fourth embodiment of the probe according to the invention. In this fourth embodiment, a depression 221 is formed in one side surface of the distal end portion 202, and the ultrasonic vibrating element 206 is embedded in the depression 221. Moreover, in the depression 221, a reflection mirror 222 is accommodated at a position opposite to the ultrasonic vibrating element 206. The reflection mirror 222 functions to reflect the ultrasonic wave emitted from the ultrasonic vibrating element 206 to a radial direction of the distal end portion 202 and to reflect the ultrasonic echo supplied from the body cavity toward the ultrasonic vibrating element 206. Moreover, a rotation shaft 223 is projected from the reflection mirror 222. The rotation shaft 223 is introduced into the hole 209 formed in the distal end portion 202 at a position opposite to the ultrasonic vibrating element 206. In the hole 209, the ball bearings 210 and 211 for supporting the rotation shaft 223 and the ultrasonic motor 214 are arranged as is the same as the third embodiment.

Figure 14:
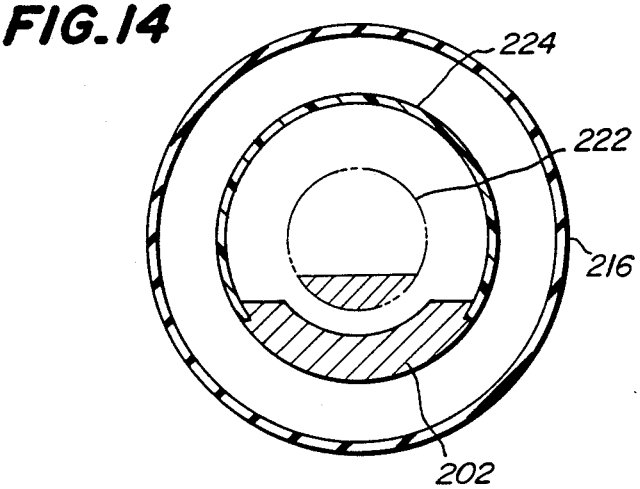
FIG. 14 is a cross sectional view showing an embodiment cut along A—A line of the embodiment shown in FIG. 13.

Moreover, in the depression 221, a liquid having a good ultrasonic transmitting function is filled, and the opening of the depression 221 is closed by a plug plate 224. FIG. 14 is a cross sectional view showing an embodiment cut along A—A line of the embodiment shown in FIG. 13.

In the fourth embodiment mentioned above, since the ultrasonic reflection mirror 222 for reflecting an ultrasonic wave emitted from the ultrasonic vibrating element 206 toward the body cavity and for reflecting the ultrasonic echo reflected from the body cavity toward the ultrasonic vibrating element 206 is rotated by the ultrasonic motor 214, the operation section for effecting the ultrasonic scanning operation can be made small in size as is the same as the third embodiment.

Figure 15:
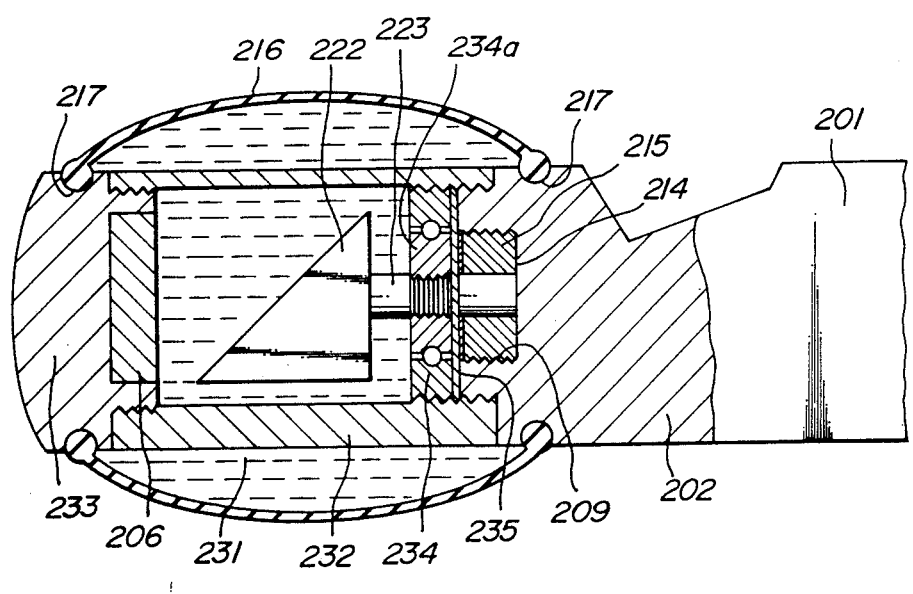
FIG. 15 is a cross sectional view illustrating a fifth embodiment of the probe according to the invention.

FIG. 15 is a cross sectional view showing a fifth embodiment of the probe according to the invention. In the fifth embodiment, an ultrasonic scanning head 231 connected to the distal end portion 202 comprises a tubular member 232 projected from the distal end portion 202 in the axis direction thereof, and a distal cover 233 for closing an opening of the tubular member 232. Moreover, the ultrasonic vibrating element 206 is embedded in an end surface of the distal cover 233, and the ultrasonic reflection mirror 222 is accommodated in an inner space of the tubular member 232 at a position opposite to the ultrasonic vibrating element 206. Further, in the inner space for accommodating the reflection mirror 222, a liquid having good ultrasonic transmitting function is filled.

The rotation shaft 223 of the reflection mirror 222 is rotatably supported by a ball bearing 234, and a tip portion of the rotation shaft 223 is introduced into the hole provided in the end surface of the distal end portion 202. Moreover, the ultrasonic vibrator 215 of the ultrasonic motor 214 is screwed in the hole 209. The end surface of the ultrasonic vibrator 215 is the same as that of the distal end portion 202 and is arranged opposite to an inner lathe 234a of the ball bearing 234. Moreover, a partition 235 for isolating liquid-tightly the inner space of the tubular member 232 from the hole 209 is provided between the ultrasonic vibrator 215 and the inner lathe 234a. The partition 235 is formed by a thin and plastic material so as not to absorb the vibration of the ultrasonic vibrator 215, and functions to transmit the vibration of the ultrasonic vibrator 215 to the inner lathe 234a accurately.

In the fifth embodiment, since the ultrasonic vibrator 215 is isolated liquid-tightly from the inner space of the tubular member 232 in which the liquid is filled by means of the partition 235, the liquid is not intruded into the ultrasonic motor 214 at all and a rotation efficiency of the ultrasonic motor 214 can be improved.

In the fifth embodiment mentioned above, the inner lathe of the ball bearing is used for the rotor of the ultrasonic motor, but use may be made of a rotor arranged apart from the inner lathe. In this case, the rotor can be provided inside the ultrasonic vibrator.

Figure 16A:
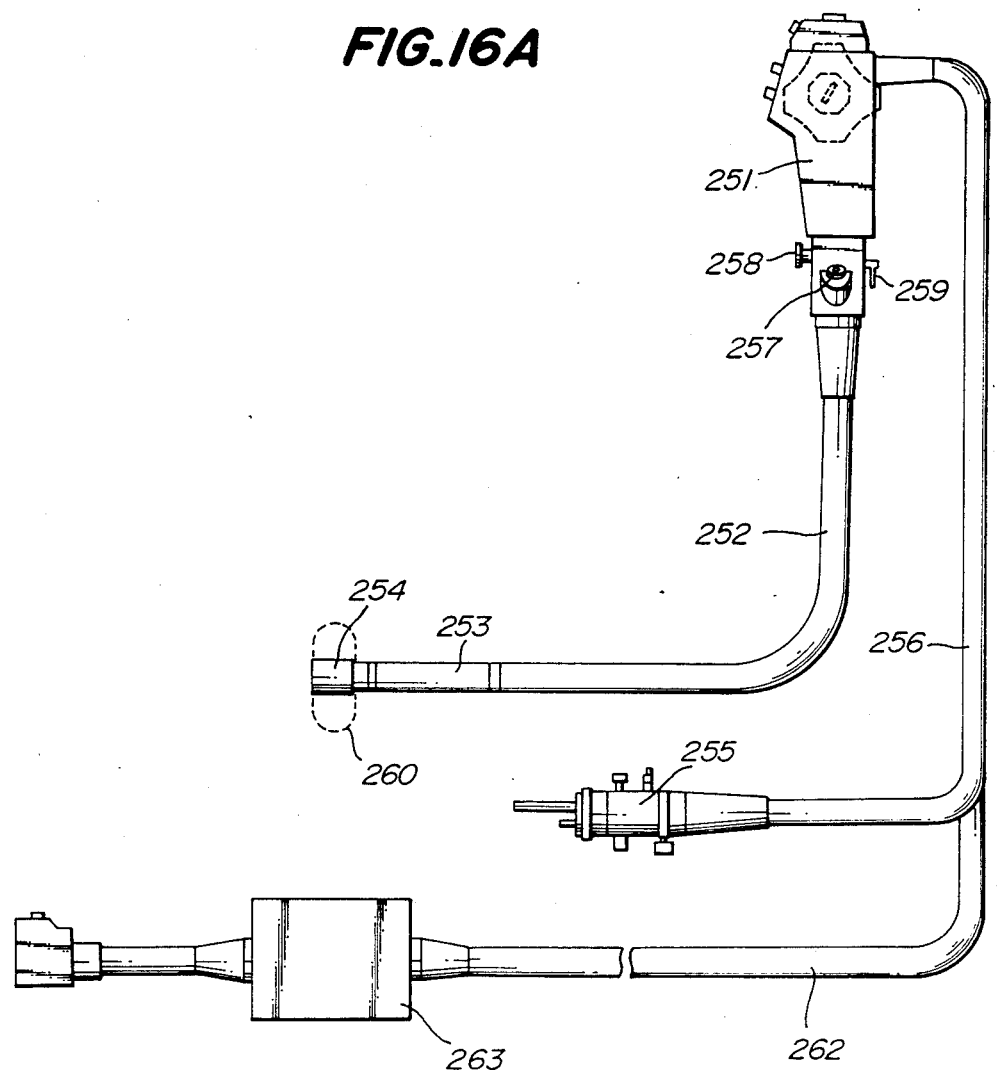
FIG. 16A is a schematic view depicting a sixth embodiment of the probe according to the invention.
Figure 16B:
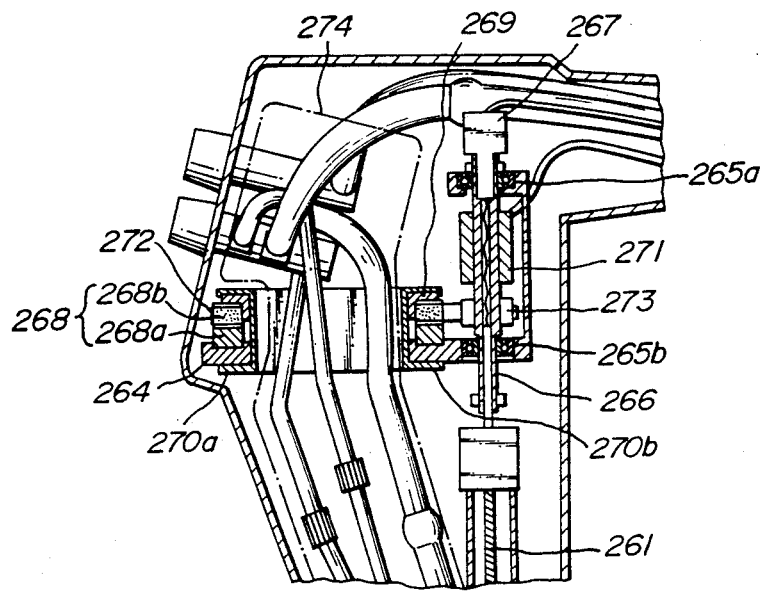
FIG. 16B is a schematic view showing an inner construction of an operation section of the probe shown in FIG. 16A.

FIG. 16A is a schematic view showing a sixth embodiment of the probe according to the invention, and FIG. 16B is a schematic view illustrating an inner construction of an operation section of the probe depicted in FIG. 16A. In the embodiment shown in FIG. 16A, an insertion section 252 to be inserted into the body cavity, a flexible portion 253 and a distal end portion 254 are connected to an operation section 251 in the order. Moreover, an universal code 256 having a connector 255 at its distal end is connected to the operation section 251. Further, a cable 262 having an amplifier 263 is divided from the universal code 256.

Various members such as optical system, channel, operation wire etc. are provided in a portion from the operation section 251 to the insertion section 252, and another members such as air supply channel, water supply channel, light transmission means etc. are also provided in a portion from the connector 255 to the distal end portion 254 via the universal code 256, so that the observation in the body cavity can be performed. An opening 257 for the forceps is arranged in a connection portion between the operation section 251 and the insertion section 252 and the opening 257 is connected to the channel in the insertion section 252. Therefore, it is possible to insert an operation member such as froceps from the opening 257 so as to effect various operations. Moreover, a water supply opening 258 for the balloon and a suction change-over lever 259 are provided in the connection portion so as to effect water supply and water suction operations with respect to a balloon 260 arranged to the distal end portion 254.

Further, an ultrasonic vibrating element is rotatably provided in the distal end portion 254, and a rotation of a drive section provided in the operation section 251 is supplied to the ultrasonic vibrating element through a flexible shaft 261 (rotation shaft) extended in the insertion section 252. The ultrasonic vibrating element is electrically connected to an observation device through a cable 262 divided from the universal code 256. Moreover, a handle is arranged in the operation section 251 so as to direct the distal end portion 254 to a desired direction by bending the flexible portion 253.

FIG. 16B is an inner construction of the operation section 251. In this embodiment, use is made of an ultrasonic motor 268 as the driving member, but the other type of motor can be used preferably. In FIG. 16B, a shaft 266 (rotation shaft) is rotatably supported by bearings 265a and 265b fixed to a base 264. One end of the shaft 266 is connected to the flexible shaft 261 extended toward the ultrasonic vibrating element, and the other end thereof is connected to a rotary transformer 267 electrically connected with the ultrasonic vibrating element provided in the distal end portion 254 via a cable arranged in the flexible shaft 261. Moreover, a rotary encoder 271 for detecting the rotation of the shaft 266 is provided around the shaft 266.

On the contrary, on the base 264, an ultrasonic motor 268 comprising a ring-shaped stator 268a and a ring-shaped rotor 268b is fixed beside the shaft 266 by means of a spacer 269, angle plates 270a and 270b. The rotation of the rotor 268b is supplied to a pulley 273 fixed to the shaft 266 by means of a timing belt 272, and thus the shaft 266 is rotated. Moreover, endoscope operation mechanisms 274 surrounded by one dotted chain line in FIG. 16B are installed in the operation section by utilizing a space formed in the ultrasonic motor 268. The endoscope operation system includes a member for supplying or sucking an inert gas in or from an object to be observed via a tube and a member for supplying water or air therein. An operation of the ultrasonic endoscope mentioned above will be explained. At first, a specific voltage is applied to the stator 268a of the ultrasonic motor 268. Then, the rotor 268b starts to rotate and the rotation of the rotor 268b is supplied to the pulley 273 via the timing belt 272, so that the shaft 266 is rotated. Further, the rotation of the shaft 266 is transmitted to the ultrasonic vibrating element provided in the distal end portion 254 via the flexible shaft 261, and the ultrasonic vibrating element is rotated. The rotary encoder 271 generates a rotation detection signal during the rotation of the shaft 266, and the ultrasonic wave is generated by supplying an electric signal to the ultrasonic vibrating element from the observation device via the rotary transformer 267. Then, the ultrasonic wave emitted from the distal end portion is projected to the object, and an echo reflected on the object is received by the ultrasonic vibrating element. The ultrasonic echo is converted into electric signals by the ultrasonic vibrating element, and the electric signals are supplied to the observation device via the rotary transformer 267 to display an ultrasonic image.

Figure 17:
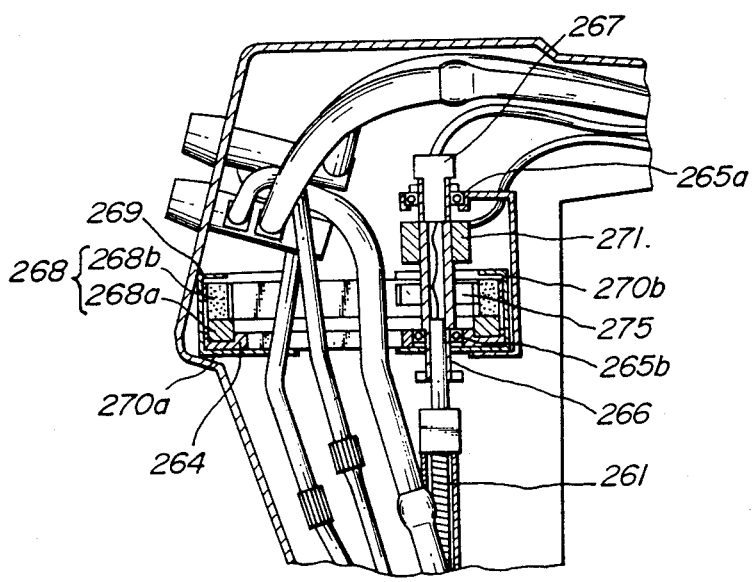
FIG. 17 is a schematic view illustrating a seventh embodiment of an inner construction of the operation section according to the invention.

FIG. 17 is a schematic view showing a seventh embodiment of an inner construction of the operation section of the probe according to the invention. In this embodiment, a rotation shaft mechanism is also arranged in the space formed in the ultrasonic motor together with the endoscope operation mechanisms. In FIG. 17, the ultrasonic motor 268 is fixed to the base 264 by means of the spacer 269, angle plates 270a and 270b, and the shaft 266 (rotation shaft) is rotatably supported in an inner space of the ultrasonic motor 268 by means of the bearings 265a and 265b. The rotation of the rotor 268b of the ultrasonic motor 268 is supplied to the shaft 266 via a gear 275 secured to the shaft 266. The other constructions of this seventh embodiment are the same as those of the sixth embodiment mentioned above.

In this case, when a predetermined voltage is applied to the stator 268a of the ultrasonic motor 268, the rotor 268b starts to rotate and the rotation of the rotor 268b is supplied to the shaft 266 via the gear 275, so that the shaft 266 is rotated. The rotation of the shaft 266 is further transmitted to the ultrasonic vibrating element via the flexible shaft 261 (rotation shaft), and the ultrasonic vibrating element is rotated. The operation for displaying the ultrasonic image in the observation device is the same as that of the sixth embodiment.

The present invention is not limited to the sixth and seventh embodiments, but various modifications are possible. In the embodiments mentioned above, use is made of the ultrasonic motor, but use may be made of the other type of motors. Further, in the sixth embodiment, use may be made of the other power transmitting means such as gear instead of the timing belt.

As mentioned above, in the sixth and seventh embodiments mentioned above, since the heavy drive section for driving the ultrasonic vibrating element is installed in the operation section, the operationability of the ultrasonic endoscope can be improved and an accurate diagnosis using the ultrasonic image can be achieved.

FIG. 18 is a cross sectional view showing an eighth embodiment of the probe according to the invention, wherein an ultrasonic motor 304 is arranged in a distal end portion 301. In this embodiment, an ultrasonic vibrating element 302 is rotated by the ultrasonic motor 304 through a shaft 303, and functions to transmit and receive the ultrasonic wave through transparent outer member 301a. A rotor 305 and a stator 306 of the ultrasonic motor 304 are arranged coaxially with respect to a center axis 307 of the distal end portion 301 which is further arranged coaxially with respect to the shaft 303 of the ultrasonic vibrating element 302. Therefore, when a driving signal is supplied to a piezoelectric element of the rotor 305 through a drive signal line 310, the stator 306 is rotated in a predetermined direction at a predetermined speed, and thus the ultrasonic vibrating element 302 can be rotated for the scanning operation. Moreover, an ultrasonic image signal is supplied through an image signal line 309. Further, an image guide 308 is arranged in the distal end portion perspectively with respect to the center axis 307. The endoscope mentioned above is so called as the endoscope of oblique observation type.

As mentioned above, the ultrasonic vibrating element 302 can receive directly the rotation power of the ultrasonic motor 304 without using the flexible shaft extended in the insertion section, and thus the ultrasonic vibrating element 302 can be rotated in regardless of the bending state of the insertion section. Moreover, since the ultrasonic motor 304 is connected coaxially with respect to the shaft 303 of the ultrasonic vibrating element 302, the rotation power can be transmitted effectively and the ultrasonic endoscope can be made small in size. Further, since the flexible shaft is not extended in the insertion section, the flexibility of the insertion section can be maintained preferably.

FIG. 19 is a cross sectional view showing a ninth embodiment of the probe according to the invention, wherein an image guide 308a is faced to a tip of the distal end portion to see an image in a forwarding direction, which is called as an endoscope of straight observation type. In this embodiment, an ultrasonic vibrating element 302a is provided in a cylindrical supporting member 311, and the supporting member 311 is rotatably supported by a ball bearing 312 and a sliding bearing. A rotor 305a and a stator 306a of an ultrasonic motor 304a are arranged coaxially with respect to a center axis 307a of the insertion section, and the rotor 305a is connected to the ultrasonic vibrating element 302a via the supporting member 311. Moreover, a numeral 310a is a drive signal line for supplying the driving signal to the piezoelectric element of the rotor 305a, and a numeral 309a is an image signal line for supplying the ultrasonic image signal to the observation device.

In this ninth embodiment, since the image guide 308a etc. are arranged in a cylindrical portion of the ultrasonic motor 304a, an outer diameter of the insertion section can be made small in size even in the endoscope of straight observation type. The other effects based on the other constructions are the same as those of the eighth embodiment.

FIG. 20 is a cross sectional view showing a tenth embodiment of the probe according to the invention, which is a modification of the eighth embodiment, illustrated in FIG. 18. In this embodiment, an ultrasonic motor 304b is arranged in a side of a tip of a distal end portion 301b as compared with an ultrasonic vibrating element 302b, and a shaft through which an image signal line 309b is arranged is connected to a rear end of the ultrasonic vibrating element 302b. A numeral 313 represents a slip ring device. The effects of this embodiment is the same as those of the eighth embodiment illustrated in FIG. 18.

FIG. 21 is a cross sectional view showing an eleventh embodiment of the probe according to the invention, which is a modification of the ninth embodiment illustrated in FIG. 19. In this embodiment, as is the same as the tenth embodiment mentioned above, an ultrasonic motor 304c is arranged in a side of a tip of a distal end portion 301c as compared with an ultrasonic vibrating element 302c. The effects of this embodiment is the same as those of the ninth embodiment illustrated in FIG. 19.

In the embodiments illustrated in FIGS. 18 to 21, the ultrasonic motor is arranged in the distal end portion, but it is possible to provide the ultrasonic motor in the operation section (not shown in these figures) of the probe. In this case, it is necessary to use the flexible shaft for transmitting the rotation power to the ultrasonic vibrating element, which is extended in the insertion section. However, even in this case, if the ultrasonic motor is arranged coaxially with respect to the insertion section, the bending operation of the insertion section is not affected to the rotation of the ultrasonic vibrating element.

As mentioned above, according to the eighth to eleventh embodiments, since the ultrasonic motor is arranged coaxially with respect to the insertion section, the rotation power can be transmitted to the ultrasonic vibrating element effectively, and the ultrasonic scanning operation can be carried out accurately. Moreover, since use is made of the ultrasonic motor as the driving means, an outer diameter of the insertion section can be made small.

Figures 22, 23:
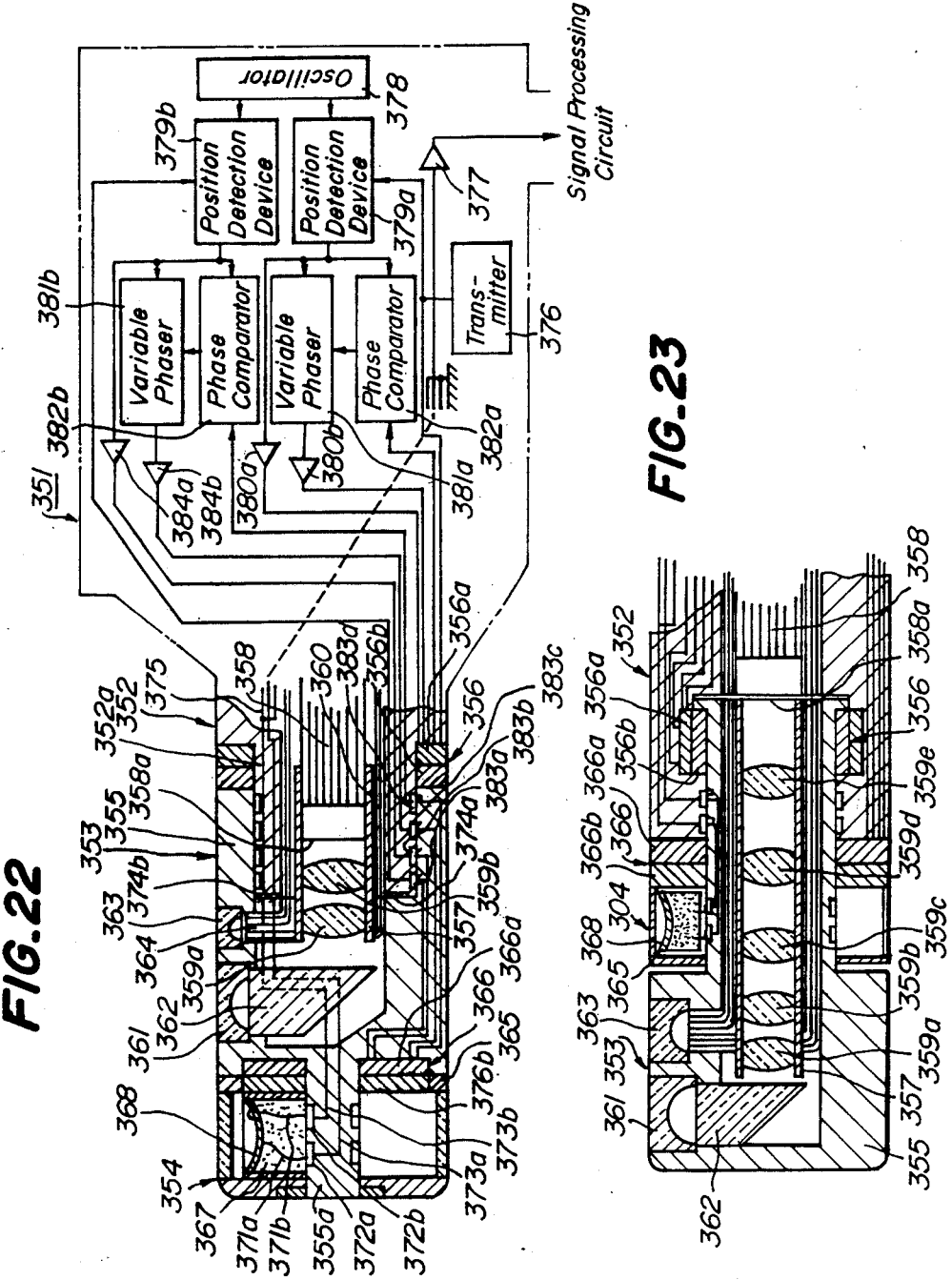
FIGS. 22 and 23 are schematic views showing a twelfth embodiment and a thirteenth embodiment of the probe according to the invention respectively.

FIG. 22 is a schematic view showing a twelfth embodiment of the probe according to the invention. In this embodiment, a distal end portion comprises a hard tip part 352 and an ultrasonic vibration part 354. An observation part 353 is rotatably provided in the hard tip part 352 with respect to an axis of the distal end portion and the ultrasonic vibration part 354 is rotatably provided to a tip of the hard tip part 352 with respect to the axis of the distal end portion. A projection part 352a is also arranged to the tip of the hard tip part 352 along the axis of the distal end portion, and the observation part 353 is rotatably arranged to the projection part 352a with respect to the axis of the distal end portion. Then, a first ultrasonic motor 356 comprising a stator 356a provided in the hard tip part 352 and a rotor 356b provided in a main body 355 of the observation part 353 in such a manner that the stator 356a is brought into contact with the rotor 356b is arranged so as to rotate the observation part 353.

Moreover, a tubular metal member 357 is provided to the projection part 352a of the hard tip part 352, and an incident end portion of an image guide 358 and lenses 359a, 359b constructing an observation optical system are provided in the tubular metal member 357. Further, an emit end portion of a first light guide 360 constructing a lighting optical system is arranged all around the tubular metal member 357. Furthermore, an observation window 361 and a prism 362 constructing the observation optical system are provided in the main body 355 of the observation part 352, and thus an optical image of the object can be focused on an incident end surface 358a of the image guide 358 through the observation window 361, the prism 362 and the lenses 359a, 359b. Moreover, a lighting window 363 constructing the lighting optical system and an emit end portion of a second light guide 364 are provided in the main body 355 of the observation part 352, and an incident end portion of the second light guide 364 is arranged slidably around the tubular metal member 357 in such a manner that the incident end portion of the second light guide 364 is always faced to the emit end portion of the first light guide 360 even if the main body 355 is rotated with respect to the tubular metal member 357. Therefore, a lighting light from the first light guide 360 can be introduced to the object through the second light guide 364 and the lighting window 363.

A projection part 355a extended along the axis of the distal end portion is arranged to a tip of the main body 355, and the ultrasonic vibration part 354 is provided rotatably to the projection part 355a with respect to the axis of the distal end portion. Moreover, a second ultrasonic motor 366 comprising a stator 366a provided in the main body 355 and a rotor 366b provided in a main body 365 of the ultrasonic vibration part 354 in such a manner that the stator 366a is brought into contact with the rotor 366b is arranged so as to rotate the ultrasonic vibration part 354.

A damper member 367 connected to the rotor 366b of the second ultrasonic motor 366 is provided in the main body 365 of the ultrasonic vibration part 354 so as to rotate the ultrasonic vibration part 354 in a slidable manner on the projection part 355a of the main body 355, and an ultrasonic vibrating element 368 is provided to the damper member 367 so as to project the ultrasonic wave in a direction perpendicular to the axis of the distal end portion.

Further, a position detection sensor for detecting an observation position of the optical image obtained from the observation part 353 is provided in the first ultrasonic motor 356, and a position detection sensor for detecting an ultrasonic wave projecting position of the ultrasonic vibrating element 368 is provided in the second ultrasonic motor 356.

Lead wires 371a and 371b of the ultrasonic vibrating element 368 are connected to a transmitter 376 through slip rings 372a, 372b provided on a circumferential surface of the projection part 355a of the main body 355, connection wires 373a, 373b, slip rings 374a, 374b provided on a circumferential surface of the projection part 352a of the hard tip part 352 and a coaxial cable 375. Therefore, it is possible to project the ultrasonic wave on the object by driving the ultrasonic vibrating element 368, and further it is possible to display the ultrasonic image on a display device by supplying the echo signal received by the ultrasonic vibrating element 368 to a signal processing circuit through an amplifier 377.

Moreover, an oscillator 378 is arranged for driving the first ultrasonic motor 356 and the second ultrasonic motor 366, and an output signal of the oscillator 378 is supplied to position detection devices 379a and 379b. The output signal of the position detection device 379a is supplied to one of electrodes of the first ultrasonic motor 356 through an amplifier 380a and is supplied to the other electrodes of the first ultrasonic motor 356 through variable phaser 381a and an amplifier 380b, so that the first ultrasonic motor 356 is rotated. Further, an output signal of a phase detecton electrode of the first ultrasonic motor 356 is supplied to a phase comparator 382a, and a phase difference between the output signal and a signal applied to the other electrodes is detected in the phase comparator 382a. Then, a phase of the signal applied to the other electrodes is compensated for by the variable phaser 381a in response to the thus obtained phase difference so as to control the rotation speed of the first ultrasonic motor 356, and an output signal of the position detection sensor is supplied to the position detection device 379a so as to control the observation position of the optical image.

Signal lines of the second ultrasonic motor 366 are connected respectively to slip rings 383a to 383d provided on a circumferential surface of the projection part of the hard tip part 352, and desired signals are supplied through the slip rings 383a to 383d. That is to say, an output signal of the position detection device 379b is supplied to one of electrodes of the second ultrasonic motor 366 through an amplifier 384a and the slip ring 383b and is supplied to the other electrodes of the second ultrasonic motor 366 through a variable phaser 381b, an amplifier 384b and the slip ring 383c, so that the second ultrasonic motor 366 is rotated. Moreover, an output signal of a phase detection electrode of the second ultrasonic motor 366 is supplied to a phase comparator 382b through the slip ring 383d, and a phase difference between the output signal and a signal applied to the other electrodes is detected in the phase comparator 382b. Then, a phase of the signal applied to the other electrodes is compensated for by the variable phaser 381b in response to the thus obtained phase difference so as to control the rotation speed of the second ultrasonic motor 366, and an output signal of the position detection sensor is supplied to the position detection device 379b through the slip ring 383a so as to control the ultrasonic wave projection position.

In the embodiment mentioned above, an ultrasonic sectional image of 360° with respect to the object can be obtained by rotating the ultrasonic vibration part 354 by means of the second ultrasonic motor 366. Moreover, when a disease portion is detected from the ultrasonic sectional image of 360° at a position apart from that of the optical image obtained by the observation part 353, the observation position of the optical image can be shifted to that of the disease portion by rotating the observation part 353 by means of the first ultrasonic motor 356 without bending the insertion section i.e. without shifting the observation position of the ultrasonic image. Therefore, an arbitral optical image in the observation portion by the ultrasonic wave can be observed by an easy operation. Moreover, since the lighting light can be always projected on the object through the first and second light guides 360, 364 and the lighting window 363, a desired part of the object can be observed optically in a sharp manner even if an amount of the lighting light is small. Further, since the rotations are performed by the ultrasonic motors 356, 366 provided in the distal end portion, an outer diameter of the insertion section can be made small.

FIG. 23 is a schematic view showing a thirteenth embodiment of the probe according to the invention. In this embodiment, the observation part 353 is arranged rotatably with respect to the hard tip part 352 by means of the first ultrasonic motor 356, and the ultrasonic vibration part 354 is arranged rotatably with respect to the hard tip part 352 and the observation part 353 by means of the second ultrasonic motor 366. Therefore, the stator 366a of the second ultrasonic motor 366 is provided on an end surface of the hard tip part 352, and the rotor 366b is provided in the main body 365 of the ultrasonic vibration part 354 in such a manner that the stator 366a is brought into contact with the rotor 366b. Moreover, the tubular metal member 357 is provided to the main body 355 of the observation part 353, and the lenses 359a to 359e are supported in the tubular metal member 357. Then, the optical image transmitting through the lenses 359a to 359e, the observation window 361 and the prism 362 is focused on the incident end surface 358a of the image guide 358 arranged in the hard tip part 352. The other constructions are the same as those of the twelfth embodiment shown in FIG. 22.

In the thirteenth embodiment mentioned above, as is the same as the twelfth embodiment, when the disease portion is detected from the ultrasonic sectional image at a position apart from that of the optical image obtained by the observation part 353, it is possible to shift the position of the optical image to that of the disease portion by rotating the observation part 353 by means of the first ultrasonic motor 356, and thus the same effects as those of the twelfth embodiment can be obtained.

The present invention is not limited to these twelfth and thirteenth embodiments mentioned above, but various modifications are possible. For example, in the embodiments mentioned above, the ultrasonic vibrating element and a tip portion of the optical unit including the observation optical system and the lighting optical system are rotated respectively by the ultrasonic motors, but it is possible to rotate them by the normal electric motor. Moreover, the ultrasonic vibrating element is fixed and the scanning operation is performed by rotating the reflection mirror on which the ultrasonic wave is projected by means of the ultrasonic motor and the electric motor. Also in the observation section, it is possible to obtain arbitrary optical images by rotating the reflection mirror. Moreover, use may be made of a solid state image sensor instead of the image guide.

Figure 24:
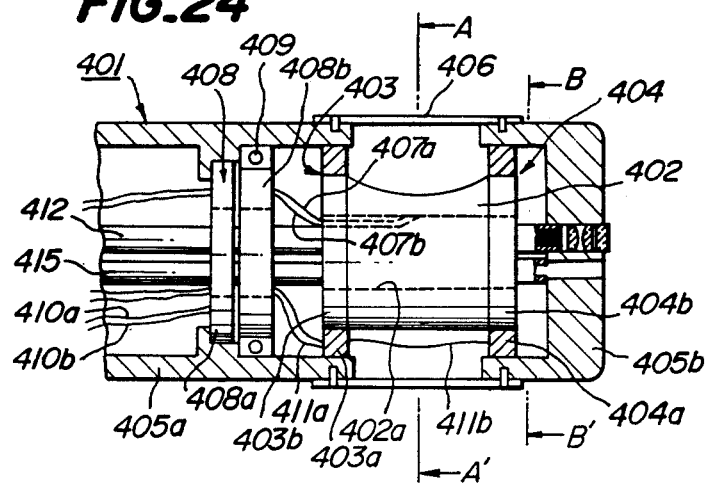
FIG. 24 is a schematic view illustrating a fourteenth embodiment of the probe according to the invention.
Figure 25:
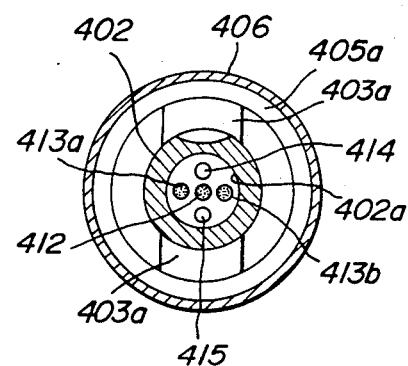
FIGS. 25 and 26 are cross sectional views depicting embodiments cut along A—A' line and B—B' line of the embodiment shown in FIG. 24 respectively.
Figure 26:
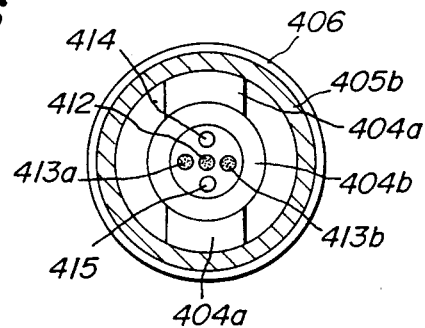

FIG. 24 is a schematic view showing a fourteenth embodiment of the probe according to the invention. Moreover, FIGS. 25 and 26 are cross sectional views illustrating embodiments cut along A—A' line and B—B' line of the embodiment shown in FIG. 24. In this embodiment, an ultrasonic vibrating element 402 is provided rotatably in a distal end portion 401 with respect to a center axis of the distal end portion, and the ultrasonic vibrating element 402 is rotated by ultrasonic motors 403 and 404 provided on both ends thereof. The ultrasonic motor 403 comprises a stator 403a provided to a support member 405a and a ring-shaped rotor 403b provided on one surface of the ultrasonic vibrating element 402. Moreover, the ultrasonic motor 404 comprises a stator 404a provided to a support member 405b and a ring-shaped rotor 404b provided on the other surface of the ultrasonic vibrating element 402. A tubular window 406 through which the ultrasonic wave emitted from the ultrasonic vibrating element 402 is projected in a direction perpendicular to the axis of the distal end portion 401 is arranged between the support members 405a and 405b.

In this embodiment, the ultrasonic vibrating element 402 is made from organic piezoelectric material such as polyvinylidene fluoride (PVDF) or its copolymer, and a through hole 402a is formed in the ultrasonic vibrating element 402 along the center axis of the distal end portion 401. In this manner, if the ultrasonic vibrating element 402 is constructed by the organic piezoelectric material, the ultrasonic vibrating element 402 having a concave lens portion can be easily formed by pressing it to a concave member, and it is not necessary to use the members such as acoustic lens, matching layer and damper member etc. Signal lines 407a and 407b of the ultrasonic vibrating element 402 are connected to a transmitting and receiving circuit not shown through a hollow rotary encoder 408. A stator 408a of the rotary encoder 408 is fixed to the support member 405a, and a rotor 408b thereof is provided rotatably to the support member 405a through a bearing 409. Then, a predetermined signal is supplied to the stator 408a through the signal lines 410a and 410b, and the rotor 408b is rotated at the same speed in the same direction as those of the ultrasonic vibrating element 402 in a synchronous manner. In this manner, the ultrasonic vibrating element 402 is rotated by the ultrasonic motors 403 and 404, and the ultrasonic wave is emitted from the ultrasonic vibrating element 402 by driving the ultrasonic vibrating element 402 to perform the ultrasonic scanning operation for the object, so that the ultrasonic sectional image can be obtained. Moreover, signal lines 411a and 411b for use in the driving operation of the ultrasonic motors 403 and 404 are extended in a through hole of the rotary encoder 408.

In the embodiment mentioned above, an image guide 412, light guides 413a and 413b, an air supply and water supply tube 414 and a forceps channel 415 are arranged through the rotary encoder 408, the ultrasonic motor 403, the through hole 402a of the ultrasonic vibrating element 402 and the ultrasonic motor 404, and distal ends of them are fixed to an end portion of the support member 405b so as to construct the endoscope of straight observation type which can observe optically the forwarding portion. Moreover, the optical system such as observation window and lens is fixed in front of the image guide 412 in the support member 405b, and a lighting window is supported by the support member 405b in front of the light guides 413a and 413b.

In this manner, since the ultrasonic vibrating element 402 is rotated by the ultrasonic motors 403 and 404 and various endoscope members are arranged through the ultrasonic motors 403, 404 and the through hole 402a of the ultrasonic vibrating element 402, the endoscope of straight observation type can be realized without making an outer diameter of the insertion section large.

In the embodiments mentioned above, use is made of the image guide, but it is possible to effect the straight observation in the forwarding direction by using the solid state image sensor instead of the image guide. In this case, signal lines of the solid state image sensor can be extended in the ultrasonic motor and the through holes of the ultrasonic vibrating element. Moreover, as for the ultrasonic vibrating element, use is made of the organic piezoelectric material, but it is possible to use a piezoelectric ceramic.

As mentioned above, according to the fourteenth embodiment, the patient can swallow the insertion section easily, and the operation of the insertion section in the body cavity can be performed easily, because the insertion section is small in size. Moreover, since the tip of the insertion section can be easily introduced to the desired portion, it is possible to effect an accurate diagnosis.

Figure 27:
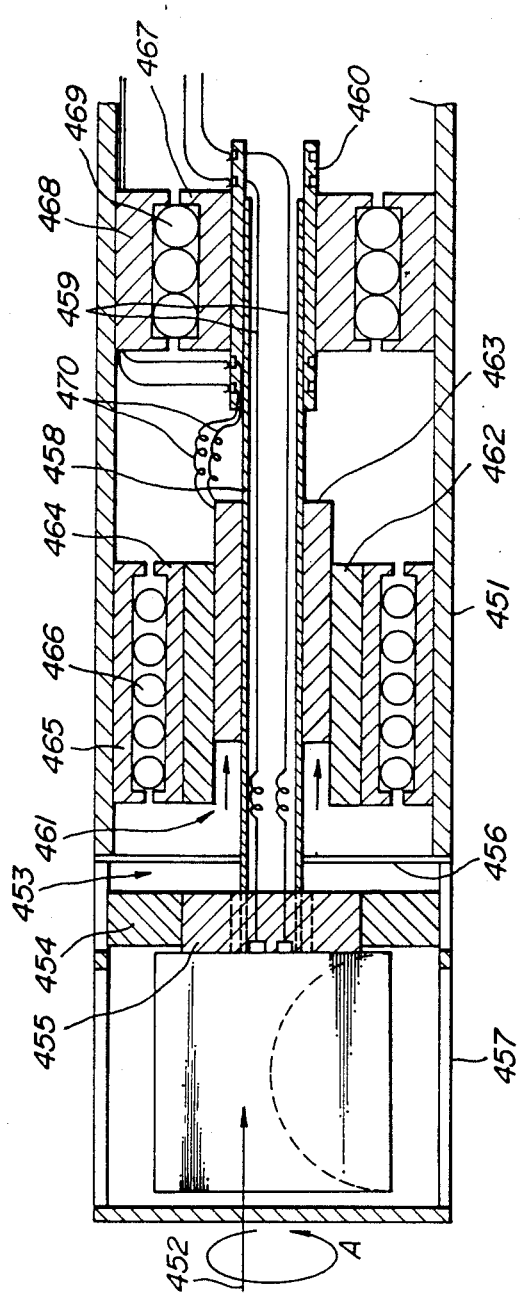
FIGS. 27 and 28 are cross sectional views showing a fifteenth embodiment of the probe according to the invention in a shrink state and an elongated state respectively.

FIG. 27 is a cross sectional view showing a fifteenth embodiment of the probe according to the invention. In this embodiment, an ultrasonic vibrating element 452 is arranged in a tip of a distal end portion 451, and is rotated in an arrow A direction with respect to a center axis of the distal end portion 451 by means of an ultrasonic motor 453. In this manner, an ultrasonic scanning operation in a direction perpendicular to the center axis is performed through a window 457. The ultrasonic motor 453 comprises a stator 454 fixed in the distal end portion 451 and a rotor 455 connected to an end portion of the ultrasonic vibrating element 452 and provided oppositely to the stator 454. When a predetermined signal is supplied to the stator 454, the rotor 455 starts to rotate and thus the ultrasonic vibrating element 452 is rotated correspondingly. Almost all the insertion section has a flexibility and the insertion section is extended to an operation section. In the distal end portion 451, a shaft 458 is arranged along the center axis thereof. One end of the shaft 458 is fixed to the ultrasonic vibrating element 452, and the other end thereof is supported by a support member 460 in a slidable manner. The support member 460 is fixed to a support member 467 which is supported by a bearing ball 469 and a fixed member 468 provided in the distal end portion 451, and thus the shaft 458 can be rotated. A signal line 470 of an ultrasonic linear motor 461 and a cable 459 of the ultrasonic vibrating element 452 are introduced to the operation section not shown through a slip ring provided in the support member 460. As for the shaft 458, use is made of a hard shaft, but it is preferable to use a flexible shaft because it permits the bending of the distal end portion 451. The ultrasonic linear motor 461 is arranged around an outer surface of the shaft 458 so as to move the shaft 458 reciprocally along the center axis of the distal end portion 451. That is to say, the ultrasonic linear motor 461 comprises a slider 463 provided to the shaft 458 and a stator 462 fixed to a support member 464 which is rotatably supported by a ball bearing 466 and a fixed member 465 fixed to the distal end portion 451, in such a manner that the stator 462 is brought into contact with the slider 463. Therefore, if the shaft 458 starts to rotate, the slider 463 and the stator 462 are rotated at the same time, because the shaft 458 is supported by a bearing constructed by the support member 464, the fixed member 465 and the bearing ball.

An elastic member 456 stretching along the center axis direction is provided between the ultrasonic motor 453 and the ultrasonic linear motor 461. The elastic member 456 is made from an elastic rubber having a hollow at its center portion.

Figure 28:
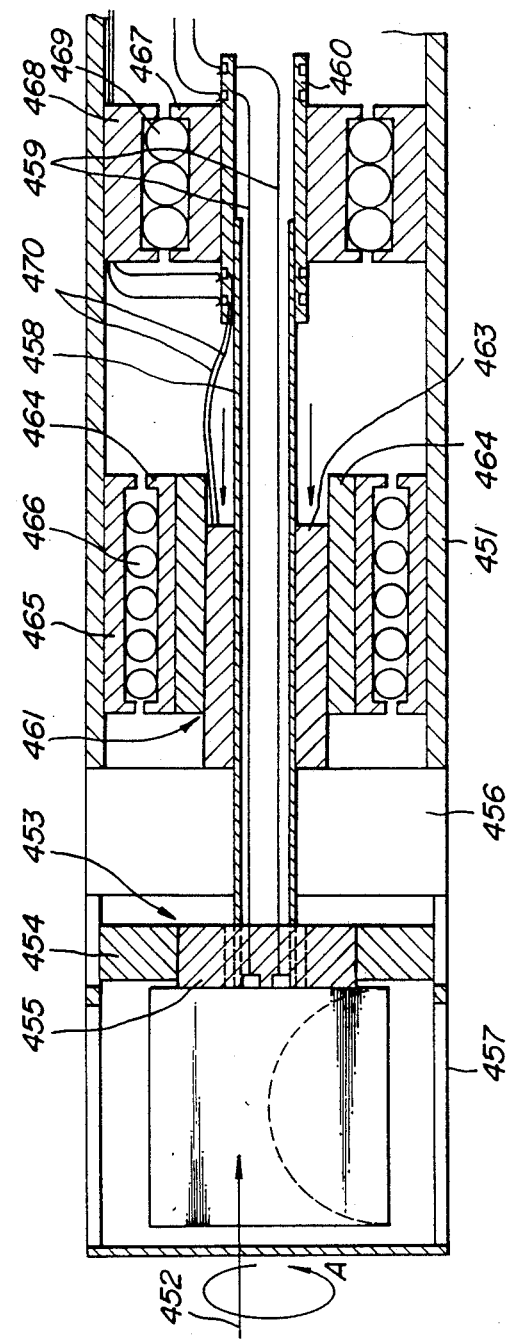

Therefore, by driving the ultrasonic linear motor 461, the distal end portion 451 becomes a shortest state illustrated in FIG. 27 and a longest state illustrated in FIG. 28.

In order to obtain three dimensional ultrasonic image data, the distal end portion 451 is first set to the shortest state shown in FIG. 27 or the longest state shown in FIG. 28, and then an ultrasonic image at this position is obtained by rotating the ultrasonic vibrating element 452. Then, the shaft 458 is moved linearly by a predetermined distance by means of the ultrasonic linear motor 461 and an ultrasonic image at this position is obtained in the same manner as that mentioned above. By repeating the same operations mentioned above, a plurality of two dimensional images along the same axis can be obtained. Therefore, the three dimensional image data can be preferably obtained by processing these two dimensional images.

The present invention is not limited to the fifth embodiment, but various modifications are possible. For example, if a bearing is provided between the shaft 458 and the rotor 455 of the ultrasonic motor 453, it is possible to fix the ultrasonic linear motor 461 in the distal end portion 451. Moreover, if the ultrasonic vibrating element 452 is not rotated, the window 457 is made longer along the center axis of the distal end portion 451 and the ultrasonic vibrating element 452 is moved reciprocally in the window 457.

As mentioned above, according to the fifteenth embodiment, since the ultrasonic vibrating element is moved accurately along the center axis of the distal end portion by means of the ultrasonic linear motor, a plurality of two dimensional images for synthesizing three dimensional ultrasonic image data can be obtained. Therefore, the ultrasonic diagnosis in the body cavity can be performed more accurately.

Figure 29:
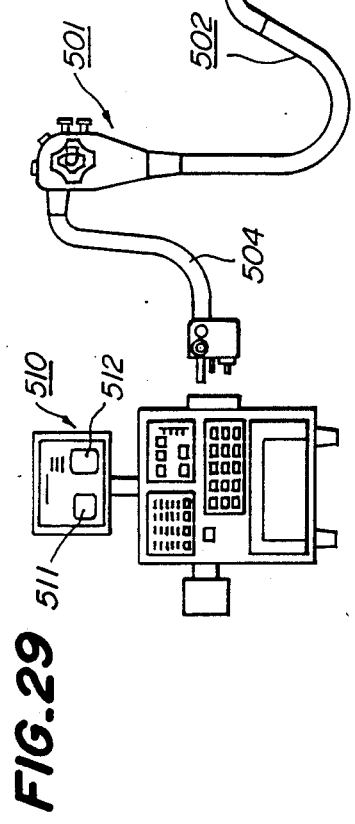
FIG. 29 is a schematic view illustrating an embodiment of an ultrasonic endoscope system and an ultrasonic video endoscope system according to the invention.

FIG. 29 is a schematic view showing a conception of an ultrasonic endoscope system and an ultrasonic video endoscope system according to the invention. In the ultrasonic endoscope system, a probe 501 comprises an insertion section 502, an operation section (handling section) 503 and a universal code 504. Moreover, a distal end portion of the insertion section 502 comprises means for obtaining an ultrasonic image such as an ultrasonic vibrating element rotated by an ultrasonic motor and preferably means for obtaining an optical image, as is the same as the embodiment mentioned above. Further, a display device 510 comprises switches for a control operation, a monitor 511 for displaying the ultrasonic image and preferably a monitor 512 for displaying the optical image.

In the ultrasonic video endoscope system, a video probe 501 comprises an insertion section, an operation section (handling section) 503 and a universal code 504. Moreover, a distal end portion of the insertion section 502 comprises means for obtaining the ultrasonic image such as the ultrasonic vibrating element connected to a driving means, and a solid state image sensor for obtaining the optical image. Further, a display device 510 comprises switches for the control operation, a monitor 511 for displaying the ultrasonic image and a monitor 512 for displaying the optical image.

Figure 30:
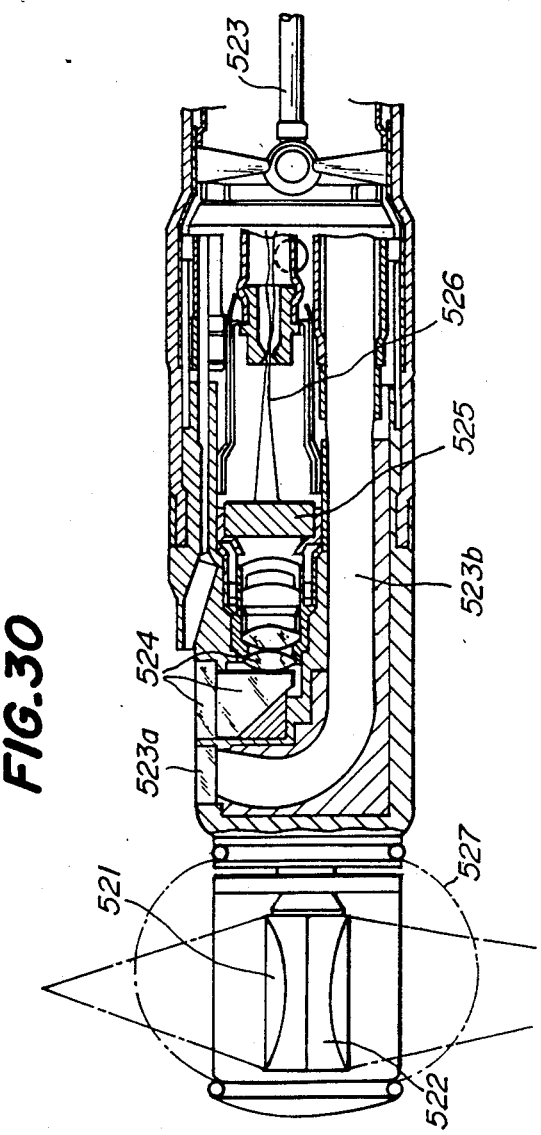
FIG. 30 is a schematic view depicting an embodiment of an insertion section of the ultrasonic video endoscope system according to the invention.

FIG. 30 is a schematic view showing an embodiment of a distal end portion of the ultrasonic video endoscope system according to the invention. In this embodiment, use is made of two ultrasonic vibrating elements 521 and 522 having different focal distances and arranged coaxially with each other as an ultrasonic wave transmitting and receiving means, and the ultrasonic vibrating elements 521 and 522 are rotated by a rotation shaft 523 extended in the insertion section 502, one end of which is connected to the ultrasonic vibrating elements 521 and 522. Moreover, as for an observation means, use is made of a light guide consisting of a lens 523a and a light guide bundle 523b extended in the insertion section 502, an objective lens 524 provided in the distal end portion of the insertion section and a solid state image sensor 525 for converting the optical image to an electric signal. The electric signal generated in the solid state image sensor 525 is supplied to the display device 510 through a cable 526. Further, a balloon 527 is arranged on an outer surface of the ultrasonic vibrating elements 521 and 522.

Figure 31:
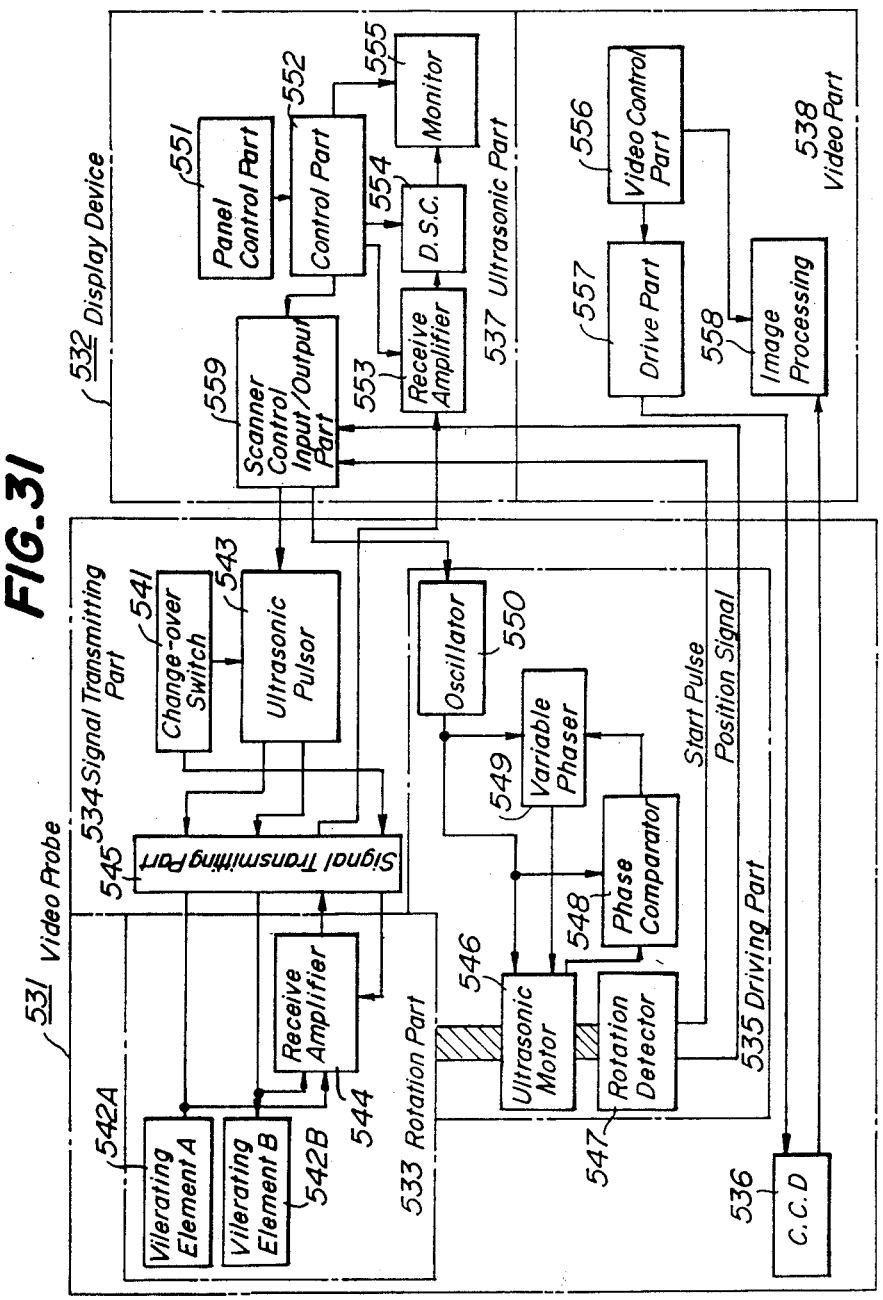
FIG. 31 is a block diagram showing an embodiment of the ultrasonic video endoscope system according to the invention.

FIG. 31 is a block diagram showing an embodiment of the ultrasonic video endoscope system according to the invention. In this embodiment, the ultrasonic video endoscope system comprises a video probe 531 and a display device 523. The video probe 531 comprises a rotation part 533, a signal transmitting part 534, a driving part 535 and a solid state image sensor 536 such as C.C.D., and the display device 532 includes an ultrasonic part 537 and a video part 538.

In the video probe 531, an ultrasonic wave generated in an ultrasonic pulsar 543 is supplied to an ultrasonic vibrating element 542A or 542B selected by a changeover switch 541, and an ultrasonic wave is projected to an object from the selected ultrasonic vibrating element 542A or 542B. The ultrasonic wave reflected on the object is received by the ultrasonic vibrating element 542A or 542B, and the thus received ultrasonic wave is converted into an electric signal. The converted electric signal is amplified by a receive amplifier 544 and is further supplied to the ultrasonic part 537 in the display device 532. A signal transmitter 545 is constructed by for example a slip ring, and is used so as not to entangle the cable even if the rotation part 533 is rotated. In this embodiment, the driving part 535 comprises an ultrasonic motor 546, a rotation detector 547, a phase comparator 548, a variable phaser 549 and an oscillator 550, and the operations thereof are the same as those of the first embodiment shown in FIG. 4.

In the display device 532, the ultrasonic image supplied from the receive amplifier 544 is displayed on a monitor 555 through a receive amplifier 553 and a D.S.C. 554 under the control of a control part 552 based on an input of a panel control part 551. Operations of the rotation part 533, the signal transmitting part 534 and the driving part 535 are controlled by the control part 552 through a scanner control input/output part 559. The optical image obtained from the solid state image sensor 536 is displayed on the monitor 555 through an image processing part 558 under the control of a video control part 556 and a sensor drive part 557.

Figure 32:
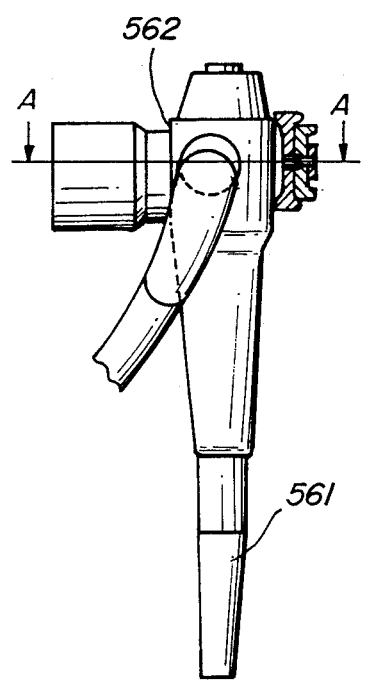
FIG. 32 is a schematic view illustrating an embodiment of an operation section of the ultrasonic video endoscope system according to the invention.
Figure 33:
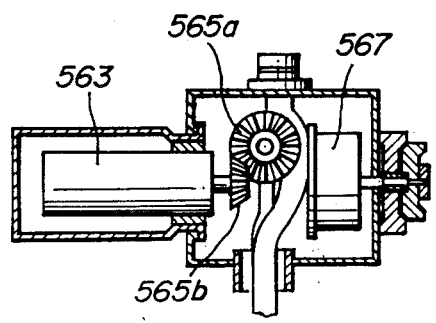
FIG. 33 is a cross sectional view depicting an embodiment cut along A—A line of the embodiment shown in FIG. 32.
Figure 34:
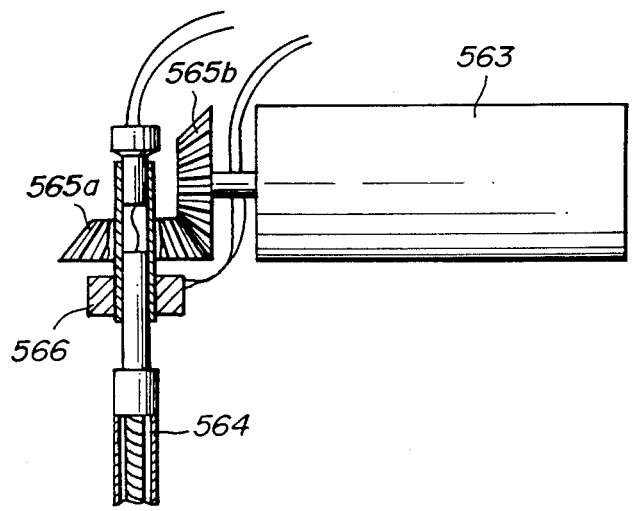
FIG. 34 is a schematic view showing an embodiment of the driving member of the embodiment shown in FIG. 33.

FIG. 32 is a schematic view showing an embodiment of an operation section of the ultrasonic video endoscope system according to the invention. Moreover, FIGS. 33 and 34 are a cross sectional view cut along A—A line of the embodiment illustrated in FIG. 32 and a schematic view depicting a main portion of the embodiment illustrated in FIG. 32. In this embodiment, an electric motor as the driving means is provided in an operation section (handling section) 562 arranged at a proximal end of an insertion section 561 of the video probe. That is to say, as shown in FIGS. 32 and 33, an electric motor 563 is arranged to a housing of the operation section 562 together with a operation mechanism 567, and a driving power transmitting member constructed by the helical gears 565a and 565b is arranged between a rotation shaft of the electric motor 563 and a flexible shaft 564 extended in the insertion section 561, one end of which is connected to the ultrasonic transmitting and receiving means, and the flexible shaft 564 can be rotated. Moreover, a rotation detector 566 is arranged around the flexible shaft 564 so as to detect a rotation state. In this embodiment, it is possible to use the ultrasonic motor instead of the electric motor 563.

Figure 35:
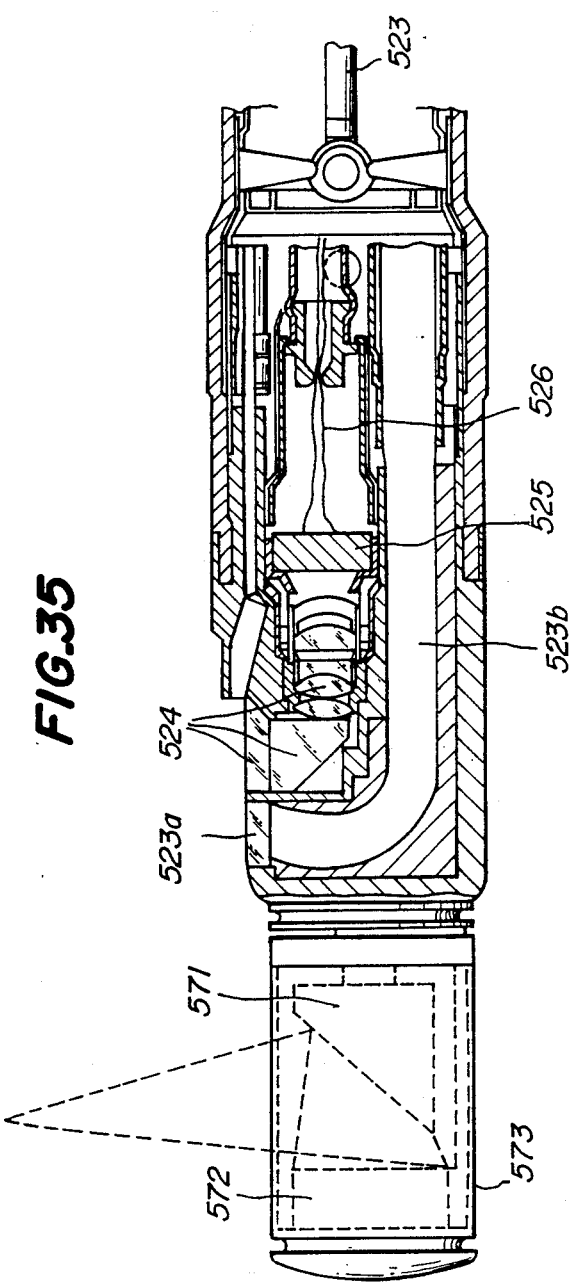
FIG. 35 is a schematic view illustrating another embodiment of the insertion section of the ultrasonic video endoscope system according to the invention.

FIG. 35 is a schematic view showing another embodiment of the insertion section of the ultrasonic video endoscope system according to the invention. In this embodiment, an ultrasonic reflection mirror 571 is fixed to the rotation shaft 523, and the scanning operation is performed by rotating the ultrasonic reflection mirror 571 instead of rotating the ultrasonic vibrating element itself. That is to say, an ultrasonic vibrating element 572 is fixed to a hard tip part 573, and the ultrasonic reflection mirror 571 provided rotatably to the hard tip part 573 is connected to the rotation shaft 523.

What is claimed is:

1. A probe for observing an ultrasonic image, comprising:
    an insertion section for being inserted into an object to be observed,
    an ultrasonic transmitting and receiving means provided in a distal end portion of said insertion section for transmitting an ultrasonic wave to the object and for receiving the ultrasonic wave reflected on the object, in which the received ultrasonic wave is converted into an electric signal, and
    an ultrasonic driving motor for rotating said ultrasonic transmitting and receiving means to effect a mechanical scanning operation using the ultrasonic wave with respect to the object to be observed, said ultrasonic motor comprising a rotor connected to said ultrasonic transmitting and receiving means and a stator secured to one of said insertion section and a member fixed relative to said insertion section, said rotor being in contact with said stator.

2. A probe according to claim 1, wherein said ultrasonic driving motor is arranged in the distal end portion of said insertion section.

3. A probe according to claim 2, wherein said stator is fixed to a hard tip part of the distal end portion.

4. A probe according to claim 3, wherein an ultrasonic vibrating element provided in said ultrasonic transmitting and receiving means is rotatably secured to the hard tip part, and the rotor of the ultrasonic driving motor is connected to the ultrasonic vibrating element.

5. A probe according to claim 4, wherein an ultrasonic linear motor is provided in the distal end portion, and the ultrasonic vibrating element and the ultrasonic driving motor are moved integrally along a rotation shaft of the ultrasonic vibrating element by means of the ultrasonic linear motor.

6. A probe according to claim 4, wherein a rotation shaft connected to a holder in which the ultrasonic vibrating element is fixed is rotatably secured to the hard tip part via a bearing, and one of the rotation shaft and the bearing is used for the rotor while the other of them is used for the stator.

7. A probe according to claim 3, wherein said ultrasonic transmitting and receiving means comprises an ultrasonic vibrating element fixed to the hard tip part and an ultrasonic reflection mirror secured rotatably to the hard tip part, and the rotor of the ultrasonic driving motor is connected to the ultrasonic reflection mirror of said ultrasonic transmitting and receiving means.

8. A probe according to claim 7, wherein the rotor is constructed as a part of the reflection mirror.

9. A probe according to claim 3, wherein the rotor is coaxially arranged with respect to the stator.

10. A probe according to claim 1, wherein an operation section is arranged in a proximal end of said insertion section, and said ultrasonic driving motor is arranged in the operation section.

11. A probe according to claim 10, further comprising a rotation shaft extended in said insertion section, one end of said rotation shaft being connected to said ultrasonic transmitting and receiving means, and wherein said rotor is connected to a proximal end of the rotation shaft and said member to which said stator is fixed is a housing of said operation section.

12. A probe according to claim 11, wherein an ultrasonic vibrating element provided in said ultrasonic transmitting and receiving means is rotatably secured to a hard tip part of the distal end portion, and the rotor of the ultrasonic driving motor is connected to the ultrasonic vibrating element of said ultrasonic transmitting and receiving means through the rotation shaft.

13. A probe according to claim 11, wherein the rotation shaft is integrally formed with the rotor.

14. A probe according to claim 11, wherein said ultrasonic transmitting and receiving means comprises an ultrasonic vibrating element of said ultrasonic transmitting and receiving means, fixed to a hard tip part of the distal end portion and an ultrasonic reflection mirror secured rotatably to the hard tip part, and the rotor of the ultrasonic driving motor is connected to the ultrasonic reflection mirror of said ultrasonic transmitting and receiving means through the rotation shaft.

15. A probe according to claim 11, wherein the rotor and the stator are arranged coaxially with respect to the rotation shaft.

16. A probe according to claim 11, wherein center axes of the rotor and the stator are shifted with respect to an axis of the rotation shaft, and a rotation power transmitting means is arranged between the rotor and the rotation shaft.

17. A probe according to claim 1, wherein a drive section is arranged between said insertion section and an operation section provided in a proximal end of said insertion section, and said ultrasonic driving motor is arranged in the drive section.

18. A probe according to claim 17, further comprising a rotation shaft extended in said insertion section, one end of said rotation shaft being connected to said ultrasonic transmitting and receiving means, and wherein said rotor is connected to a proximal end of the rotation shaft and said member to which said stator is fixed is a housing of said drive section.

19. A probe according to claim 18, wherein an ultrasonic vibrating element provided in said ultrasonic transmitting and receiving means is rotatably secured to a hard tip part of the distal end portion, and the rotor of the ultrasonic driving motor is connected to the ultrasonic vibrating element of said ultrasonic transmitting and receiving means through the rotation shaft.

20. A probe according to claim 18, wherein the rotation shaft is integrally formed with the rotor.

21. A probe according to claim 18, wherein said ultrasonic transmitting and receiving means comprises an ultrasonic vibrating element of said ultrasonic transmitting and receiving means, fixed to a hard tip part of the distal end portion and an ultrasonic reflection mirror secured rotatably to the hard tip part, and the rotor of the ultrasonic driving motor is connected to the ultrasonic reflection mirror of said ultrasonic transmitting and receiving means through the rotation shaft.

22. A probe according to claim 18, wherein the rotor and the stator are arranged coaxially with respect to the rotation shaft.

23. A probe according to claim 18, wherein center axes of the rotor and the stator are shifted with respect to an axis of the rotation shaft, and a rotation power transmitting means is arranged between the rotor and the rotation shaft.

24. A probe according to claim 4 or 7, further comprising an observation means for obtaining an optical image of the object to be observed.

25. A probe according to claim 24, wherein a through hole is arranged in the ultrasonic vibrating element, and said observation means is extended in the through hole.

26. A probe according to claim 24, wherein a second ultrasonic motor is arranged in the distal end portion spaced apart from the ultrasonic driving motor and said observation means is rotated by the second ultrasonic motor.

27. A probe according to claim 24, wherein said observation means comprises a light guide extended in said insertion section, an objective lens provided in the distal end portion, and an image guide extended in said insertion section.

28. A probe according to claim 1, wherein said ultrasonic transmitting and receiving means has a plurality of ultrasonic vibrating elements having different focal distances with each other.

* * * * *